US006803200B2

(12) United States Patent
Xia et al.

(10) Patent No.: US 6,803,200 B2
(45) Date of Patent: Oct. 12, 2004

(54) COMPOSITIONS AND METHODS FOR THE RELEASE OF NUCLEIC ACID MOLECULES FROM SOLID MATRICES

(75) Inventors: Jiu-Lin Xia, Germantown, MD (US); Mindy D. Goldsborough, Gaithersburg, MD (US); Michael A. Connolly, Gaithersburg, MD (US); Gulilat Gebeyehu, Potomac, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 10/012,443

(22) Filed: Dec. 12, 2001

(65) Prior Publication Data

US 2002/0090635 A1 Jul. 11, 2002

Related U.S. Application Data

(60) Provisional application No. 60/254,583, filed on Dec. 12, 2000.

(51) Int. Cl.[7] .............................. C12Q 1/68; C12N 7/02; C07H 21/02; C07H 21/04; B01D 11/00; B01D 11/04; C02F 1/26; C02F 1/44
(52) U.S. Cl. ........................ 435/6; 435/239; 536/23.1; 210/634; 210/656; 210/658; 210/198.2
(58) Field of Search .................... 435/6, 239; 536/23.1; 210/634, 656, 658, 198.2

(56) References Cited

U.S. PATENT DOCUMENTS

| | | | |
|---|---|---|---|
| 4,055,469 A | 10/1977 | Smoke et al. | |
| 4,419,509 A | 12/1983 | Hsiung | |
| 4,965,349 A | 10/1990 | Woo et al. | |
| 5,098,603 A | 3/1992 | Perlman | |
| 5,208,160 A | * 5/1993 | Kikyotani et al. | .......... 435/270 |
| 5,428,148 A | 6/1995 | Reddy et al. | |
| 5,496,562 A | 3/1996 | Burgoyne | |
| 5,514,789 A | 5/1996 | Kempe | |
| 5,518,651 A | 5/1996 | Reddy et al. | |
| 5,580,859 A | 12/1996 | Felgner et al. | |
| 5,738,829 A | 4/1998 | Kempe | |
| 5,756,705 A | 5/1998 | Wang | |
| 5,773,590 A | 6/1998 | Hart | |
| 5,888,397 A | 3/1999 | Rogers et al. | |
| 2002/0143166 A1 | 10/2002 | Pires et al. | |

FOREIGN PATENT DOCUMENTS

| | | |
|---|---|---|
| EP | 0 323 152 A2 | 7/1989 |
| WO | WO 99/38962 | 8/1999 |
| WO | WO 99/39009 | 8/1999 |
| WO | WO 99/39010 | 8/1999 |

OTHER PUBLICATIONS

Cantor, C. R. et al., "Biophysical Chemistry. Part I. The Conformation of Biological Molecules", W. H. Freeman and Co., San Francisco, pp. 163–164 (1980).*

Costa et al., "Cloning and Analysis of PCR–generated DNA fragments", in "PCR Primer. A laboratory Manual", Cold Spring Harbor Laboratory Press, pp. 555–580 (1995).*

Westman, E. et al., "Separation of DNA restriction fragments by Ion–Exchange Chromatography on FPLC Columns on FPLC Columns Mono P and Mono Q", Anal. Biochem., vol. 166, pp. 158–171 (1987).*

Sigma Catalog, p. 402 (1993).*

Kasai, K., "Size–dependent chromatographic separation of nucleic acids", J. Chromatogr., vol. 618, pp. 203–221 (1993).*

Kim, Y. et al., "Rapid Pulsed Field Capilary Electrophoretic Separation of Megabase Nucleic Acids", Anal. Chem., vol. 67, pp. 784–786 (1995).*

Huber, C. G., "Micropellicular stationary phases for high–performance liquid chromatography of double–stranded DNA", J. Chromatogr. A, vol. 806, pp. 3–30 (1998).*

Sambrook, J., et al., eds., "Chapter 9. Analysis and Cloning of Eukaryotic Genomic DNA," in: *Molecular Cloning. A Laboratory Manual*, Cold Spring Harbor Laboratory Press, Cold Spring Harbor, N.Y., pp. 9.2–9.14 (1989).

Seltzer, W.K., et al., "Screening for Cystic Fibrosis: Feasibility of Molecular Genetic Analysis of Dried Blood Specimens," *Biochem. Med. Meta. Biol.* 46:105–109, Academic Press, Inc. (1991).

Skogerboe, K.J., et al., "Genetic Screening of Newborns for Sickle Cell Disease: Correlation of DNA Analysis with Hemoglobin Electrophoresis," *Clin. Chem.* 37:454–458, American Association for Clinical Chemistry, Inc. (1991).

McEwen, J.E. and Reilly, P.R., "Stored Guthrie as DNA 'Banks'," *Am. J. Hum. Genet*. 55:196–200, The University of Chicago Press (1994).

Reddy, M.P., et al., "Fast Cleavage and Deprotection of Oligonucleotides," *Tetra. Lett.* 35:4311–4314, Elsevier Science Ltd (1994).

Rogers, C. and Burgoyne, L., "Bacterial Typing Storing and Processing of Stabilized Reference Bacteria for Polymerase Chain Reaction without Preparing DNA—An Example of an Automatable Procedure," *Anal. Biochem.* 247:223–227, Academic Press (1997).

(List continued on next page.)

*Primary Examiner*—Gary Benzion
*Assistant Examiner*—Teresa Strzelecka
(74) *Attorney, Agent, or Firm*—Sterne, Kessler, Goldstein & Fox P.L.L.C.

(57) ABSTRACT

The present invention relates to compositions and methods for releasing nucleic acid molecules from solid matrices. The invention further relates to compositions and methods for purifying and isolating nucleic acid molecules from biological materials such as animal tissues and plant matter. The methods of the invention can be readily adapted for rapid processing of multiple samples. Thus, the invention further provides automated methods for the purification of nucleic acid molecules from numerous samples. The invention also relates to kits for removing nucleic acid molecules from solid matrices.

77 Claims, 6 Drawing Sheets

OTHER PUBLICATIONS

Gait, M.J., et al., "Oligoribonucleotide synthesis," in: *Oligonucleotides and Analogues*, Eckstein, F., ed., Oxford University Press, Oxford, UK, pp. 25–47 (1991).

Gibco BRL, "DNA Isolation," in: *Product Catalogue and Reference Guide*, Life Technologies, Gaithersburg, MD, pp. 14–2 to 14–18 and 18–36 to 18–37 (1995–1996).

Jinks, D.C., et al., "Molecular genetic diagnosis of sickle cell disease using dried blood specimens on blotters used for newborn screening," *Hum. Genet.* 81:363–366, Springer–Verlag (1989).

"Ac–dC," *Glen Research*, Online Product Information, 6 pages, Glen Reasearch, available at www.glenres.com/ProductFiles/Information/1015.html (May 20, 1999).

"Alternatives to Expedite Monomers," *Glen Research*, Online Product Information, 2 pages, Glen Research, available at www.glenres.com/ExtraPages/Alternatives.html (May 20, 1999).

Ausubel, F., et al., eds., "Chapter 16. Protein Expression," in: *Current Protocols in Molecular Biology*, John H. Wiley & Sons, Inc., Summerset, NJ pp. 16.0.1–16.21.9 (1997).

Boal, J.H., et al., "Cleavage of oligodeoxyribonucleotides from controlled–pore glass supports and their rapid deprotection by gaseous amines," *Nucl. Acids Res.* 24:3115–3117, Oxford University Press (1996).

Burgoyne, L.A., "Convenient DNA Collection and Processing: Disposable Toothbrushes and FTA™ Paper as a Non–threatening Buccal–Cell Collection Kit Compatible with Automatable DNA Processing," *8th International Symposium on Human Identification*, 2 pages, abstract available at wysiwyg://667/http://www/proega.com/geneticidproc/ussymp8proc/ab17.html (1997).

Crea, R. and Horn, T., "Synthesis of oligonucleotides on cellulose by a phosphotriester method, " *Nucl. Acids Res.* 8:2331–2348, IRL Press Ltd. (1980).

\* cited by examiner

| 40ng | 0.1ng | 1%EtAM | 0.9%EtAM | 0.8%EtAM | 0.7%EtAM |
|---|---|---|---|---|---|
| 20ng | 0.04ng | 1%EtAM | 0.9%EtAM | 0.8%EtAM | 0.7%EtAM |
| 10ng | 0.6%EtAM | 0.5%EtAM | 0.4%EtAM | 0.3%EtAM | 0.2%EtAM |
| 4ng | 0.6%EtAM | 0.5%EtAM | 0.4%EtAM | 0.3%EtAM | 0.2%EtAM |
| 2ng | 0.1%EtAM | 0.05% EtAM | 0.025% EtAM | 0.01% EtAM | 0.005% EtAM |
| 1ng | 0.1%EtAM | 0.05% EtAM | 0.025% EtAM | 0.01% EtAM | 0.005% EtAM |
| 0.4ng | 0.0025% EtAM | 0.001% EtAM | 0.0005% EtAM | 0.00025% EtAM | TE |
| 0.2ng | 0.0025% EtAM | 0.001% EtAM | 0.0005% EtAM | 0.00025% EtAM | Negative |

FIG.3

COMPOSITIONS AND METHODS FOR THE RELEASE OF NUCLEIC ACID MOLECULES FROM SOLID MATRICES

FIELD OF THE INVENTION

The present invention relates to compositions and methods for releasing nucleic acid molecules from solid matrices. The invention further relates to compositions and methods for purifying and isolating nucleic acid molecules from biological materials such as animal tissues and plant matter.

BACKGROUND OF THE INVENTION

It is desirable in many instances to generate and analyze nucleic acid molecules samples obtained from numerous individual entities and/or organisms of populations. Often, such samples are used to identify the genotypes of individuals which reside either in the same or different geographic locations. Thus, the collection and analysis of samples are often employed to determine the genotypes of individual members of populations. Such analyses generally result in the generation of data relating to both the individuals from which the samples are obtained and the populations as a whole.

The collection and analysis of samples which contain nucleic acid molecules from populations of organisms are often performed to obtain genotype data from viral, plant and animal populations. One example of a situation where genotype analysis of large numbers of individuals of members vof populations is commonly performed is where data regarding the genotypes of plants in a geographic location is sought. These data may be generated to determine the spread rate of particular plant strains or to identify genetically modified plants which either have been grown from seeds sold to farmers or are the progeny of plants grown from such seeds.

A number of companies currently sell genetically modified plants and seeds derived from these plants. In some cases, these seeds are sold under the condition that the purchasers, generally farmers, repurchase seeds from their suppliers instead of growing plants from seeds which are obtained from plants grown from purchased seeds. Further, a number of consumer groups, as well as governmental organizations, have objected to the sale of agricultural products prepared from genetically modified plants.

In each instance described immediately above, genotype analyses can be performed to identify genetically modified plants. Such analyses often begin with the collection of large numbers of plant samples obtained in rural settings. Thus, there is a need for methods which allow for the collection and convenient storage of large numbers of samples containing nucleic acid molecules derived from plants which can then be used for genotype analyses.

In other situations, genotype analyses are performed on samples derived from animals (e.g., humans) to generate data related, again, to either individuals or populations of which these individuals are members. Further, genotype analyses performed on samples derived from either animals or plants may be used to obtain data relating to entities associated with these organisms. Examples of such associated entities include viruses such as Human Immunodeficiency Viruses (HIVs). In particular, genotype analyses of HIV populations can be performed using nucleic acid molecules obtained from human blood samples. Due to the rapid rate with which HIVs alter their genomes, genotype analyses have been employed to track the spread and regional predominance of various viral strains.

The use of filter paper (e.g., Whatman 3MM filter paper) provides an inexpensive method for the collection, shipment, and storage of samples which contain nucleic acid molecules (e.g., RNA, plasmids, viral vectors and chromosomal DNA). This is especially the case when samples are collected in remote areas where there is no access to refrigeration.

One example, of a filter paper based medium used for the collection, shipment, and storage of blood samples is FTA® paper, which is composed of cellulose material impregnated with (i) a monovalent weak base; (ii) a chelating agent; (iii) an anionic detergent; and, optionally, (iv) uric acid or a urate salt. FTA® paper can be used to store human genomic DNA, for example, in the form of dried spots of whole blood, the cells of which lyse after making contact with the paper. Stored at room temperature, genomic DNA on FTA® paper is reported to be stable for at least 7.5 years. (Burgoyne et al., CONVENTIONAL DNA COLLECTION AND PROCESSING: DISPOSABLE TOOTHBRUSHES AND FTA® PAPER AS A NON-THREATING BUCCAL-CELL COLLECTION KIT COMPATIBLE WITH AUTOMATABLE DNA PROCESSING, $8^{th}$ International Symposium on Human Identification, Sep. 17–20, 1997.) Thus, the placement of nucleic acid samples on filter paper (e.g., FTA® paper) offers a compact archival system compared to glass vials or plastic tubes located in precious freezer space.

DNA from blood spots has been used in newborn screening programs to identify genetic mutations implicated in several diseases and to provide a means for identifying military personnel. (See, e.g., Seltzer et al., *Biochem. Med. Metab. Biol.* 46:105–109 (1991); Jinks et al., *Hum. Genet.* 81:363–366 (1989); Skogerboe et al., *Clin. Chem.* 37:454–458 (1991); McEwen et al., *Am. J. Hum. Genet.* 55:196–200 (1994).)

The storage of blood samples on dried filter paper has the additional advantage of pathogen inactivation. More specifically, HIV, as well as a number of other infectious agents, are believed to lose viability upon drying. Further, nucleic acid molecules obtained from these dried blood spots, as well as other dried samples containing nucleic acid molecules, can also be used to isolate and reverse transcribe messenger-RNA (mRNA).

The spotting of bacterial nucleic acids on filter paper can also be used as part of a sample storage and retrieval system. Recently, Rogers and Burgoyne characterized samples of several bacterial strains of Staphylococcus and *Escherichia coli* stored on FTA® paper by PCR-ribotyping. (Rogers et al., *Anal. Biochem.* 247:223 (1997).)

Before analysis of nucleic acids captured by filter papers, washing steps generally need to be performed to remove stabilizing chemicals, if present, and cellular inhibitors of enzymatic reactions. Since DNA, for the most part, remains with the paper through these washing steps, manipulations to purify such nucleic acids are simplified and amenable to automation.

Several methods have been developed for releasing nucleic acids from materials such as FTA® paper. For example, Burgoyne demonstrated that purified plasmid DNA, stored on paper encased in polystyrene, can be recovered using a uric acid solution. (Burgoyne, U.S. Pat. No. 5,496,562, the entire disclosure of which is incorporated herein by reference.) Another method for nucleic acid release employs a buffer containing a chelating agent in an aqueous solution. (See, e.g., PCT Publications WO 99/39010, WO 99/38962, and WO 99/39009, each of which is incorporated herein by reference.)

The invention provides methods for releasing DNA from solid matrices which are relatively simple in comparison to methods currently in use in the art. Further, the DNA released by methods of the invention can be used directly in a number of processes (e.g., genotyping analyses).

SUMMARY OF THE INVENTION

The present invention relates to compositions and methods for the removal of nucleic acid molecules (e.g., DNA) from solid matrices. In particular, the methods of the invention employ releasing reagents to facilitate the release of nucleic acid molecules. The invention further provides compositions relating to these methods.

The present invention also relates to methods for purifying and/or isolating nucleic acid molecules.

In one general aspect, the invention provides methods for removing nucleic acid molecules from solid matrices comprising contacting the solid matrices with releasing reagents which comprise one or more alkanol amines.

In another general aspect, the invention provides methods of purifying and/or isolating nucleic acid molecules comprising:
(a) contacting the nucleic acid molecules with solid matrices under conditions which favor adherence, attachment, association, and/or binding (covalently or non-covalently) of the nucleic acid molecules to the solid matrices: and
(b) contacting the solid matrices containing the bound nucleic acid molecules with releasing reagents comprising one or more alkanol amines, under conditions which favor release of the nucleic acid molecules from the solid matrices. In a related aspect, the methods of the invention further comprise collecting the releasing reagents containing nucleic acid molecules which have been released from the solid matrices.

In specific embodiments, solid matrices used in methods of the invention comprise compounds that prevent or inhibit degradation of nucleic acid molecules, such as one or more weak bases, one or more chelating agents, one or more anionic surfactants, one or more anionic detergents, uric acid, and/or one or more urate salts.

In other specific embodiments, solid matrices used in the methods of the invention are cellulose based matrices or micromesh synthetic plastic matrices. In specific embodiments of the invention, the solid matrix is either a filter paper (e.g., Whatman 3MM paper) or an FTA® paper.

In yet other specific embodiments, the alkanol amine present in releasing reagents used in methods of the invention comprises an ethanolamine. In particular, the ethanolamine may be mono-ethanolamine, di-ethanolamine, or tri-ethanolamine.

In related embodiments, releasing reagents used in methods of the invention comprise more than one ethanolamine (e.g., two or three ethanolamines).

In certain embodiments, releasing reagents used in methods of the invention are aqueous solutions.

In specific embodiments, releasing reagents used in the methods of the invention have a pH which falls within the range of from about 8.3 to about 13 or from about 10 to about 12. In specific embodiments of the invention, the releasing reagents have a pH of about 11.

In other specific embodiments of the invention, the one or more alkanol amines are present in the releasing reagents at concentrations of from about 0.01% to about 5% (vol./vol.), from about 0.01% to about 3% (vol./vol.), from about 0.01% to about 1% (vol./vol.), or from about 0.1% to about 1% (vol./vol.).

In additional embodiments, solid matrices which contain nucleic acid molecules are incubated with releasing reagents for a time period ranging from about 1 to about 180 minutes, from about 1 to about 120 minutes, from about 10 to about 60 minutes, or from about 10 to about 30 minutes.

In further embodiments, solid matrices which contain nucleic acid molecules are incubated with releasing reagents at about 65° C. to about 100° C. or about 90° C. to about 100° C.

In certain embodiments, the methods of the invention comprise separating released nucleic acid molecules from the releasing reagents.

In additional embodiments, nucleic acid molecules released from solid matrices using methods of the invention comprise vectors (e.g., plasmids, artificial chromosomes, etc.). Similarly, nucleic acid molecules released from solid matrices using methods of the invention may comprise nucleic acid molecules of cells or viruses (e.g., cellular or viral genomic DNA, mitochondrial DNA, chloroplast DNA, etc.).

In another aspect, the invention includes nucleic acid molecules which are purified and/or isolated by methods of the invention. In specific embodiments, the nucleic acid molecules purified and/or isolated by methods of the invention may used in molecular biological processes (e.g., may be amplified by PCR). In a related aspect, the invention is further directed to methods of making recombinant host cells comprising introducing nucleic acid molecules produced by methods of the invention.

In an additional aspect, the invention provides methods for separating RNA from DNA comprising:
(a) contacting solid matrices with samples which contain RNA and DNA;
(b) contacting solid matrices of (a) with washing solutions under conditions sufficient to remove the RNA while the DNA is retained (for example, by washing the solid matrices for periods of time ranging from 1 second to 90 minutes); and
(c) contacting the washed solid matrices with releasing reagents comprising one or more alkanol amines, under conditions which favor release of the DNA from the solid matrices.

In yet another aspect, the invention provides methods for separating closed, circular nucleic acid molecules from linear nucleic acid molecules comprising:
(a) contacting solid matrices with samples which contain closed, circular nucleic acid molecules and linear nucleic acid molecules;
(b) contacting solid matrices of (a) with washing solutions under conditions sufficient to remove the closed, circular nucleic acid molecules while the linear nucleic acid molecules are retained (for example, by washing the solid matrices for periods of time ranging from 1 second to 90 minutes) and
(c) contacting the washed solid matrices with releasing reagents comprising one or more alkanol amines, under conditions which favor release of the linear nucleic acid molecules from the solid matrices.

In another aspect, the invention further provides methods for separating nucleic acid molecules on the basis of size comprising:
(a) contacting solid matrices with samples which contain nucleic acid molecules of different sizes;
(b) contacting solid matrices of (a) with washing solutions under conditions sufficient to remove smaller nucleic acid molecules while larger nucleic acid molecules are retained (for example, by washing the solid matrices for periods of time ranging from 1 second to 90 minutes); and (c) contacting the washed solid matrices with releasing reagents comprising one or more alkanol amines, under conditions which favor release of the larger nucleic acid molecules from the solid matrices.

In specific embodiments, washing solutions used in methods of the invention comprise 10 mM Tris-HCl, 1 mM EDTA (pH 7.3), water, or FTA® Purification Reagent (Invitrogen Corp., Life Technologies Division, Cat. No. 10876-019). In related specific embodiments, these washing solutions further comprise one or more detergents.

In further specific embodiments, solid matrices are washed for a time period selected from the group consisting of about 1 second, about 3 seconds, about 5 seconds, about 20 seconds, about 30 seconds, about 45 seconds, about 1 minute, about 5 minutes, about 10 minutes, and about 30 minutes.

In additional specific embodiments, when nucleic acid molecules are separated from each other on the basis of size, nucleic acid molecules having an average size of from about 1 kilobase to about 50 kilobases are separated from nucleic acid molecules having an average size of from about 100 kilobases to about 1,000 kilobases; nucleic acid molecules having an average size of from about 50 kilobase to about 100 kilobases are separated from nucleic acid molecules having an average size of from about 250 kilobases to about 500 kilobases; or nucleic acid molecules having an average size of from about 50 kilobase to about 100 kilobases are separated from nucleic acid molecules having an average size of from about 1,000 kilobases to about 4,000 kilobases.

The invention further provides compositions comprising nucleic acid molecules, solid matrices, and releasing reagents, wherein the releasing reagents comprises one or more alkanol amines.

The present invention also relates to kits for carrying out methods of the invention, as well as for preparing compositions of the invention. Thus, in one general aspect, the invention provides kits for removing nucleic acid molecules from solid matrices, the kits comprising (1) one or more releasing reagents of the invention and (2) one or more components selected from the group consisting of:

(a) at least one solid matrix;

(b) at least one apparatus for applying samples to solid matrices;

(c) at least one apparatus for cutting solid matrices into sections which contain samples; and (d) at least one washing solution.

In specific embodiments, the apparatus for applying samples to solid matrices comprises a pipette (e.g., PIPETEMAN™ Models P-2, P-10, P-20, P-100, P-200, etc., Rainin Instrument Company, Inc. Rainin Road, Box 4026, Woburn, Mass., 01888). In a related embodiment, the apparatus for applying samples to the solid matrix (e.g., a hammer, device which employs a piston, etc.) results in the samples being crushed into the surface of the solid matrix. An apparatus of this type will be especially useful when the sample comprises material obtained from a plant. In another related specific embodiment, the sample application apparatus is capable of applying multiple samples to solid matrices at one time.

In additional embodiments, the apparatus for cutting solid matrices into sections produces pieces of the matrices which are of varying shapes (e.g., circular, square, rectangular, irregular, etc.).

In further additional specific embodiments, washing solutions of kits of the invention comprise 10 mM Tris-HCl, 1 mM EDTA (pH 7.3), water, or FTA® Purification Reagent (Invitrogen Corp., Life Technologies Division, Cat. No. 10876-019). In related specific embodiments, washing solutions of kits of the invention further comprise one or more detergents.

Other embodiments of the invention will be apparent to one of ordinary skill in light of what is known in the art, the following drawings and description of the invention, and the claims.

BRIEF DESCRIPTION OF THE FIGURES

FIG. 3 depicts ACES quantitation assay results, performed as described for FIG. 1, showing the effect of ethanolamine concentration on the release of DNA from FTA® paper. 10 $\mu$l of released DNA was used in this assay. The pH of all ethanolamine solutions was 11. As the concentration of ethanolamine is increased from 0.00025% to 0.025% more DNA is released from the punch. The most DNA, approximately 50 ng, is released at a concentration of 1%. At 0.2% approximately 10 ng of DNA is released. For testing purposes, ethanolamine concentrations of 0.2% and 1% were used.

DETAILED DESCRIPTION OF THE PREFERRED EMBODIMENTS

I. Definitions

Figure 1:
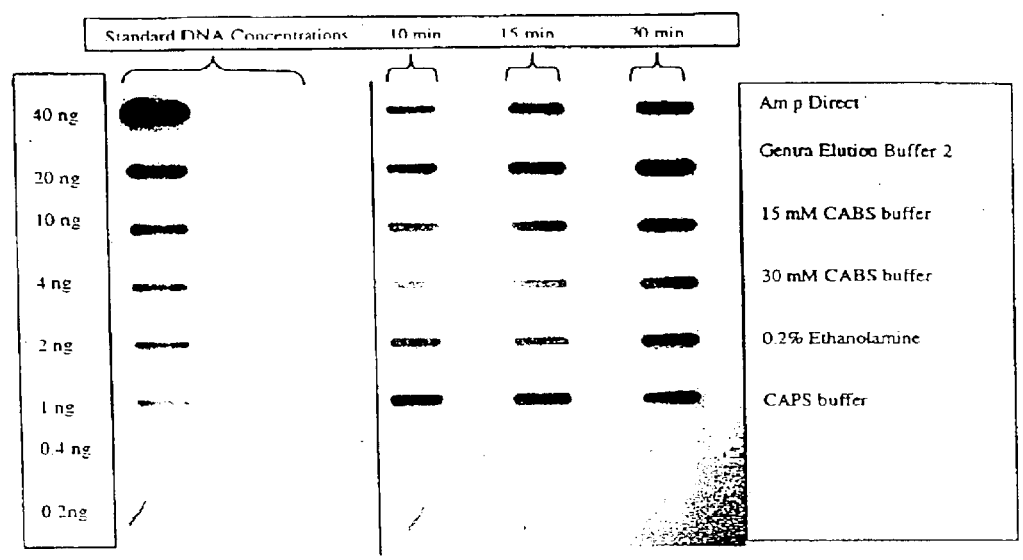
FIG. 1 depicts the results of a DNA quantitation assay performed using an ACES™ 2.0+ Human DNA Quantitation System (Invitrogen Corp., Life Technologies Division, Cat. No. 10294-015). The nylon membrane shown in FIG. 1 was prepared according to the manufacturers instructions using probe supplied with the System. The results demonstrate the ability of different reagents to release DNA from 2 mm blood punches of FTA® paper upon heating for 10–20 minutes at 100° C. All reagents tested released 50–100 ng of DNA per 2 mm punch after heating for 20 minutes. Heating time had very little effect on the 3-(cyclohexylamino)-1-propane sulfonic acid (CAPS) buffer with approximately the same amount of DNA being released at all heating times.
Figure 2:
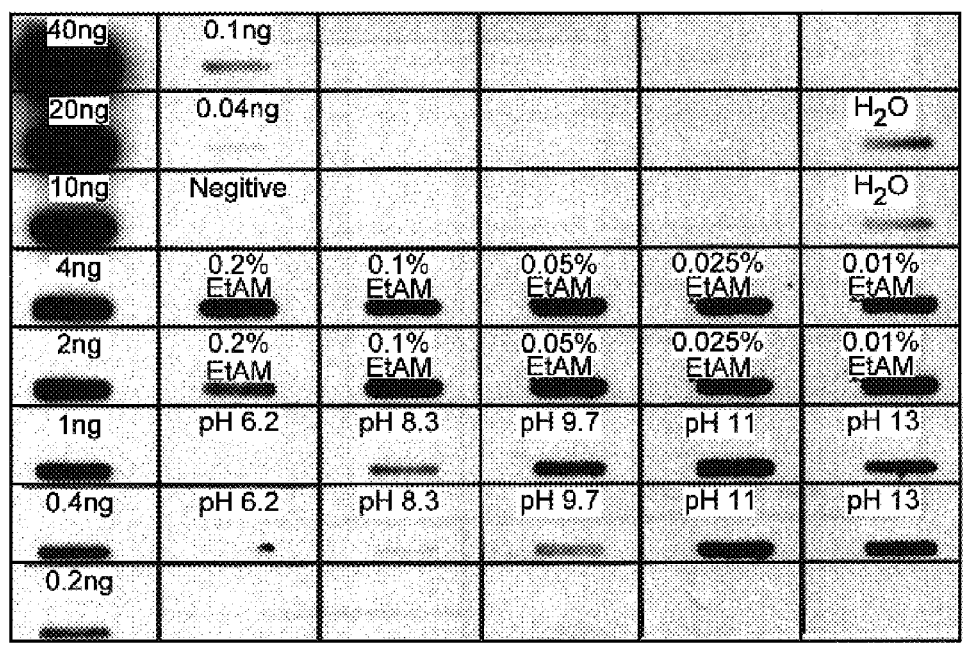
FIG. 2 depicts ACES quantitation assay results, performed as described for FIG. 1, showing concentration and pH effects on the ability of ethanolamine to release DNA from FTA® paper. DNA concentrations on the left hand side of the figure are 0.2, 0.4, 1, 2, 4, 10, 20 and 40 ng. Punches were incubated in 50 $\mu$l of ethanolamine solution at 100° C. for 10 minutes. Ten $\mu$l of the released DNA was used for quantitation. Between 0.025% and 0.2%, the concentration of the ethanolamine (all at pH 11) does not have much effect on the release of DNA from the FTA® paper. However, a change in the pH does effect the efficiency of DNA release. At pH 8.3, 0.5 ng of DNA is released per punch. At pH 9.7 and pH 13, 2 ng of DNA is released per punch. At pH 11, 10 ng of DNA is released per punch. Therefore, as discussed below in Example 2, the maximum yield, in terms of amount of released DNA, was obtained at a pH of 11.

The following definitions are provided to clarify the subject matter of the present invention.

Solid Matrix: As used herein, the phrase "solid matrix" refers to any solid support to which nucleic acid molecules adhere, bind (covalently or non-covalently), attach, and/or associate with including but not limited to cellulose based materials (e.g., cellulose based filter papers) and micromesh synthetic plastic matrices. One example of such a material is FTA® paper. (Fitzco Inc., 5600 Pioneer Creek Drive, Maple Plain, Minn. 55359 USA; Invitrogen Corp., Life Technologies Division, 9800 Medical Center Drive. Rockville, Md. 20850 USA, Catalog No. 10786-036.) Other examples include Schleicher and Schuell grade 903, 704E, 402, 404, and 577 filter papers (Schleicher and Schuell, 10 Optical Avenue, Keene, N. H. 03431 USA); Whatman BFC180. No. 1, No. 40, No. 42, No. 50, and 3MM filter papers (Whatman International, LTD, Maidstone, Kent, UK); nitrocellulose: and cellulose acetate.

In many embodiments of the invention, the solid matrix used will be a cellulose based filter paper or other type of papers (e.g., laminar conglomerates obtained by pulping fibers, such as plant fibers). Solid matrices of these types are especially useful because they are relatively inexpensive and normally work well with methods of the invention.

Solid matrixes suitable for use with the invention include those which inactivate pathogenic agents (e.g., Herpes Simplex, Cytomegalovirus, Hepatitis B, Hepatitis C, etc.). This feature is especially advantageous when the sample being applied to the solid matrix is obtained from a human (e.g., saliva, buccal swab, whole blood, etc.).

Solid matrixes may also be impregnated with agents which induce Lysis of cells. Examples of such agents include anionic detergents (e.g., sodium dodecyl sulfate, sodium deoxycholate), cation detergents (e.g., cetyl trimethylammonium bromide (CTAB), cetyl pyridinium chloride (CPC), myristyltrimethyl ammonium chloride (MTAB), dioctadecyldimethyl ammonium chloride (DODMAC)) non-ionic detergents (e g., TWEEN 80, TRITON X-100), enzymes, salts, chaotropic agents (e.g., guanidine hydrochloride), and the Like.

In specific embodiment, solid matrixes may comprise glass (e.g., controlled pore glass beads) and plastics (e.g., polystyrene, polyvinylchloride, polypropylene, polyethylene, polyvinylidenedifluoride, nylon, etc.).

Solid matrixes suitable for use with the invention may be in any form or configuration including beads, filters, membranes, sheets, columns and the like.

Alkanol Amines: As used herein, the phrase "alkanol amines" refers to $C_2$–$C_{50}$ compounds which contain at least one amino group and at least one alcohol group. Examples of such compounds include N.N-dimethylethanolamine. N-methyldiethanolamine, 3-aminopropyldiethanolamine, diisopropanolamine, N-methylethanolamine, 2-(dibutylamino)ethanol, 2-(diisopropylamino)ethanol, 2-(isopropylamino)ethanol, 2-(propylamino)ethanol, 2-(tert-butylamino)ethanol, 2-benzylaminoethanol, 2-butylaminoethanol, N-phenylethanolamine, mono-ethanolamine, di-ethanolamine, and tri-ethanolamine, as well as mixtures of various alkanol amines. Alkanol amines, such as those listed above, are available from commercial suppliers such as Sigma-Aldrich Corporation, 3050 Spruce Street, St. Louis, Mo. 63103 USA. In certain embodiments, alkanol amines will not include 3-(cyclohexylamino)-2-hydroxypropanesulfonic acid (CAPSO), proteins, and/or molecules having a molecular weight over 100, 150, 200, 250, 300, 350, 400, 450, or 500.

Releasing Reagents: As used herein, the phrase "releasing reagents" refers to reagents of the invention which induce the release of nucleic acid molecules from solid matrices. Releasing reagents of the invention comprise one or more alkanol amines. Additional characteristics of releasing reagents are described below.

Nucleic Acid Molecules: As used herein, the phrase "nucleic acid molecules," refers to molecules composed chains of alternating units of phosphoric acid and deoxyribose, linked to purine and pyrimidine bases, such as DNA (e.g., RNA, cDNA, mitochondrial DNA, chloroplast DNA, genomic DNA, double minutes, artificial chromosomes, extrachromosomal elements, synthetic DNA, etc.). Representative examples of nucleic acid molecules include vectors (e.g., plasmids, yeast artificial chromosomes, mammalian artificial chromosomes, bacterial artificial chromosomes, and the like) and genomic nucleic acid molecules of prokaryotic organisms, eukaryotic organisms, and viruses (e.g., Epstein Barr virus, bovine papillomavirus 1, duck Hepatitis B viruses, Mycoplasma virus P1, etc.).

Purified: As used herein, the term "purified," when used in reference to a biological molecule (e.g., a nucleic acid) means that the molecule has been separated from some surrounding molecules and/or materials. "Purified" is thus a relative term which is based on a change in conditions in terms of molecules and/or materials in close proximity to the molecules being purified. Thus, genomic nucleic acid molecules, for example, which adhere to, attach to, bind to (covalently or non-covalently), and/or associate with solid matrices after cell lysis are considered to be purified when at least some cellular debris, proteins and/or carbohydrates are removed by washing. These same genomic nucleic acid molecules are purified again, when they are released from solid matrices using methods of the invention. The term purified is not intended to mean that the all of matter intended to be removed is removed from the molecules being purified. Thus, some amount of contaminants may be present along with the purified molecules.

For practical applications, the concentration of materials such as water, salts, and buffer are not considered when determining whether a biological molecule has been purified. Thus, as an example, nucleic acid molecules which have been separated from other biological molecules using column chromatography but have been diluted with an aqueous buffer in the process are still considered to have been purified by the chromatographic separation process.

Isolated: As used herein, the term "isolated," when used in reference to a biological molecule (e.g., a nucleic acid) means that the molecule has been separated from substantially all of the molecules and/or materials present which surround the molecule when the molecule was associated with a biological system (e.g., inside a cell). As when determining whether a biological molecule has been purified, the concentration of materials such as water, salts, and buffer are not considered when determining whether a biological molecule has been "isolated."

Average Size: As used herein, the phrase "average size" means that at least 85% of the molecules in the population are of a size which is about +/−10% of a recited value. For example, if the recited value is 100 kilobases and 90% of the members of a population of nucleic acid molecules fall within the range of 90 to 110 kilobases, then the population has an average size of 100 kilobases. Of course, the same would be true if 98% of the members of a population of nucleic acid molecules were to fall within the range of 90 to 110 kilobases.

One or More: As used herein, the phrase "one or more" means one or more than one. As one skilled in the art would recognize, the meaning of more than one will vary with the particular context. For example, when reference is made to the use of one or more ethanolamine, one skilled in the art would recognize that this means, due to the limited number of ethanolamines, one, two, or three ethanolamines, or mixtures of these ethanolamines. However, when one or more nucleic acid molecules are referred to, one skilled in the art would recognize that, due to the number of different nucleic acid molecules which can be present in a population of such molecules, the phrase "one or more" means, one, two, three, four, five, ten, twenty, thirty, fifty, one hundred, two thousand, or one million. Thus, depending on the particular situation, the phrase "one or more" means, for example, one, two, three, four, five, ten, fifteen, twenty, thirty, fifty, one hundred, two hundred, one thousand, two thousand, five thousand, ten thousand, one hundred thousand, one million, five million, ten million, fifty million, one hundred million, one billion, etc.

Vector. As used herein, the term "vector" refers to nucleic acid molecules which are capable of replicating autonomously in a host cell. Such vectors may also be characterized by having a small number of endonuclease restriction sites at which these molecules may be cut without loss of an essential biological function and into which nucleic acid molecules may be spliced to bring about its replication and cloning. Examples of vectors include plasmids, autonomously replicating sequences (ARS), centromeres, cosmids, fosmids, phagemids, bacterial artificial chromosomes (BACs), yeast artificial chromosomes (YACs), mammalian artificial chromosomes (MACs), and the like. Vectors can further provide primer sites for PCR, transcriptional and/or translational initiation and/or regulation sites, recombinational signals, replicons, etc. Further, vectors can further contain one or more selectable markers (e.g., nucleic acid molecules which confer kanamycin resistance, tetracycline resistance, amplicillin resistance, etc.) suitable for use in the identification of cells transformed or transfected with these vectors.

In specific embodiments of the invention, the term "vector" does not include nucleic acid molecules which are less than about 50, about 75, about 100, about 125, about 150, about 175, about 200, or about 250 kilobases. In other specific embodiments of the invention, the term "vector" does not include plasmids.

In accordance with the invention, any vector may be used. In particular, vectors known in the art and those commercially available (and variants or derivatives thereof) may be used in accordance with the invention. Such vectors may be obtained from, for example, Vector Laboratories Inc., Invitrogen Corp., Promega, Novagen. NEB, Clontech, Boehringer Mannheim, Pharmacia. EpiCenter, OriGenes Technologies Inc., Stratagene, Perkin Elmer, Pharmingen, and Research Genetics. Such vectors may then for example be used for cloning or subcloning nucleic acid molecules of interest. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacteriophage λ vectors, baculovirus vectors, adenovirus vectors, and retrovirus vectors), high, low and adjustable copy number vectors, vectors which have compatible replicons for use in combination in a single host (pACYC184 and pBR322), and eukaryotic episomal replication vectors (pCDM8).

Sample. As used herein, the term "sample" refers to a material which contains nucleic acid molecules and is applied to a solid matrix. Examples of samples include bacterial cells, bacterial cell homogentates, fungal cells, protist cells, viral plaques obtained from plates, viral material (e.g., DNA or RNA) isolated by cesium chloride centrifugation, human buccal swabs, human blood, purified human blood cells, blood cell homogenates, and plant materials such as leaves, roots, stems, and fruits. Thus, the term "sample" encompasses any material which contains nucleic acid molecules and is in a form which can be applied to a solid matrix.

As described below, solid materials may be directly applied to solid matrices or a liquid solution or suspension of these materials may be prepared prior to application.

Storage. As used herein, the term "storage" refers to maintaining the solid matrices, to which samples have been applied, for periods of time. Solid matrices may be stored, for example, at a constant humidity, at about 20° C. to 30° C. for five years. Lower storage temperatures may range from about 0° C. to 20° C., −20° C. to 2° C., and −80° C. to −20° C.

Other terms used in the fields of recombinant DNA technology and molecular and cell biology as used herein will be generally understood by one of ordinary skill in the applicable arts.

II. Compositions and Methods of the Invention

As noted above, solid matrices which nucleic acid molecules adhere to, attach to, bind to (covalently or non-covalently), and/or associate with have been used in the art for various applications, including storage. Further, nucleic acid molecules bound to solid matrices can be used in biochemical reactions (e.g. PCR).

The present invention relates to novel compositions and methods for the removal of nucleic acid molecules from solid matrices. In particular, the methods of the invention relate to the contacting of solid matrices to which nucleic acid molecules are bound with solutions comprising one or more (e.g. one, two, three, etc.) alkanol amines.

In one relatively specific aspect, the invention relates to the following processes and reagents for releasing nucleic acid molecules from solid matrices. A sample which contains nucleic acid molecules in aqueous solution is spotted on a solid matrix (e.g., Whatman 3MM paper, FTA® paper, etc.). The solid matrix containing the sample is then allowed to dry. The dried solid matrix is then placed in a releasing reagent comprising one or more alkanol amines (e.g. ethanolamine) and boiled for 30 minutes. The resulting solution is then cooled to room temperature and the solid matrix is removed. The solution is then diluted with 50 volumes of a PCR buffer and nucleic acid molecules are amplified by PCR using standard protocols.

Ethanolamine is one of a group of alkanol amines which are often used as buffering agents. Due to strong hydrogen bonding and hydrophobic interactions, ethanolamine is normally a viscous fluid at room temperature. Further, ethanolamine has strong affinity for —OH and –H+ groups. It also forms complexes with some metal ions in solution. All of these combined properties make this compound a superior reagent for releasing nucleic acids from solid matrices.

Ethanolamine has considerable buffer capacity at pHs around pH 10. At pH 10, most solid matrices are negatively charged due to the presence of —COOH and —Si—OH groups. While not wishing to be bound by theory, the negative charge of solid matrices at certain basic pHs is believed to result in the re Lease of nucleic acid molecules from the charged surface.

Further, ethanolamine is believed to strongly interact with nucleic acid molecules through hydrogen bonding. This interaction is believe to facilitate the extraction of nucleic acid molecules from solid matrices. In addition, ethanolamine may also share metal ions with nucleic acid molecules since both of these compounds can form soluble metal ion complexes. This is believed to result in the formation of soluble complexes of ethanolamine and nucleic acid molecules.

As discussed below, any nucleic acid molecules may be stored and later recovered using the methods and compositions of the invention. Further, nucleic acid molecules may be separated from other materials by their ability to adhere to, attach to, bind to (covalently or non-covalently), and/or associate with and then released from solid matrices. In particular, the methods and compositions of the invention relate to simple and efficient processes in which nucleic acid molecules (e.g., chromosomal DNA, vectors, viral nucleic acid molecules, etc.) are contacted with a solid matrix (e.g., FTA® paper or derivatives, variants or modifications thereof) and released using a releasing reagent. In addition, as discussed in more detail below, released nucleic acid molecules may also be separated from other cellular materials which are also released by the releasing reagent. Thus, the invention further provides methods for purifying and/or isolating nucleic acid molecules.

Solid matrices suitable for use with the invention include those which comprise an absorbent cellulose-based matrix (e.g., cellulose based paper), or a micromesh of synthetic plastic material, such as those described in U.S. Pat. No. 5,496,562, which is incorporated by reference herein in its entirety. Further, the solid matrix may be a composition comprising a weak base, a chelating agent, an anionic surfactant or anionic detergent, and, optionally, uric acid or a urate salt. FTA® paper and derivatives, variants and modifications thereof are included among such solid matrices.

In general, when samples are intended for only short term storage (e.g., time periods of less than one month or so), the solid matrix will normally not contain agents which stabilize nucleic acid molecules (e.g., agents such as chelating agents, detergents, and uric acid or urate salts). Further, when the samples are intended for only long term storage (e.g., time periods of greater than one month or so), the solid matrix will often contain agents which stabilize nucleic acid molecules.

Solid matrices suitable for use with the invention may be of any number of shapes or forms. For example, the solid matrices may be in the form of a flat sheet or packing in a tube. It will normally be advantageous to use solid matrices in a flat sheet form when large number of separate samples are used. Flat sheet and tubular packing solid matrix forms may be used for nucleic acid purification and isolation protocols employing pressurized, centrifugal, or gravity based sample and reagent flows.

Compositions and methods of the invention may be used with (1) purified nucleic acid molecules or (2) crude preparations which contain nucleic acid molecules. Thus, the invention provides methods for purifying and/or isolating nucleic acid molecules from samples (e.g., human blood, plant cell homogenates, plant cell homogenates, leaves, seeds, bacterial cells, viruses, viral plaques, etc.).

Samples suitable for use with the invention may be obtained from numerous sources. Sources from which samples suitable for use with the present invention may be obtained include buccal swabs, plant cell extracts, plant tissues, seeds, animal fluids, animal tissues, organs, bacterial cultures, fungal cultures, protozoan cultures, and viral plaques.

As noted above, one common sample applied to solid matrices is human blood. Much of the DNA present in human blood is mitochondrial and nuclear DNA of white blood cells. The application of human blood to FTA® paper, for example, results in the lysis of blood cells, adhesion of nucleic acid molecules to the paper, and the inactivation of many pathogenic agents.

In some instances, the solid matrix will be one which protects against degradation of nucleic acid molecules bound thereto and inactivates pathogens. A considerable number of agents which can be used to perform these functions are known in the art and include detergents, chelating agents, antibiotics, and enzymes (e.g., proteinases, lipases, and nucleases).

Agents used with the solid matrix will generally be selected or used in such a concentration so that they do not substantially decrease the quality of the nucleic acid molecules which are to be later released from the matrix. For example, when one seeks to obtain DNA from a solid matrix, the matrix could be treated with agents that will selectively degrade RNA. Examples of such agents include RNAses and strong bases. As is known in the art, RNA, but not DNA, undergoes hydrolysis under alkaline conditions. Alkaline conditions are also known to inhibit the growth of many microorganisms. Thus, the pH of solid matrices can be adjusted to both degrade RNA and inhibit the growth of microorganisms.

Prior to release of nucleic acid molecules using releasing reagents of the invention, solid matrices to which nucleic acid molecules have bound may be treated to remove solvents, detergents, proteins, other nucleic acid molecules (e.g., RNA when DNA is sought), salts, etc. One method currently used in the art for removing proteins from, for example, FTA® papers is phenol extraction. (See, e.g., Burgoyne, U.S. Pat. No. 5,496,562.) Further, water soluble compounds (e.g., detergents, salts, etc.) can be removed by treating matrices with aqueous solutions (e.g., deionized water). Similarly, volatile agents may be removed by exposure of matrices to air or vacuum.

Treatment of the solid matrices after sample application but before nucleic acid release will vary with the particular application. For example, in instances where the sample contains considerable quantities of contaminants such as proteins and lipids it may be advantageous to treat solid matrices with agents that either remove or degrade these materials. Further, as noted above, proteins can be removed from solid matrices by phenol extraction, optionally with a metal ion chelator such as EDTA to stabilize the phenol. (See Perlman. U.S. Pat. No. 5,098,603.) Similarly, lipids and other hydrophobic molecules can be removed by extraction with organic solvents or detergent (e.g., anionic detergents, cationic detergents, and non-ionic detergents) washes.

Solid matrices may also be treated to remove agents which are present prior to sample addition. For example, FTA® paper contains detergent which facilitates the lysing of cells contained in samples. Under some circumstances, it may be advantageous to remove the detergent prior to nucleic acid release. One method of removing this detergent is by washing the FTA® paper with water. Depending on the particular situation, other suitable washing solutions, in addition to water, include 10 mM Tris, 1 mM EDTA (pH 7.3 or 8.0) and FTA® Purification Reagent (Invitrogen Corp., Life Technologies Division, Cat. No. 10876-019).

The methods of the invention can also be used to separate nucleic acid molecules based on physical properties such as size and/or type (e.g., RNA v. DNA, plasmid v chromosomal DNA). For example, large nucleic acid molecules associate more tightly with solid matrices than small nucleic acid molecules. Further, as the size of nucleic acid molecules increases, these molecules are believed to associate more tightly with solid matrices. Thus, smaller nucleic acid molecules (e.g., plasmids) are more easily removed from solid matrices than larger nucleic acid molecules (e.g., chromosomal DNA). Further, closed, circular nucleic acid molecules, such as plasmids, often release from solid matrices during washing steps. This is so because linear nucleic acid molecules are believed to associate more tightly with solid matrices than closed, circular nucleic acid molecules. In addition, DNA is believed to associate with solid matrices more tightly than RNA.

In view of the above, the invention further provides methods for separating nucleic acid molecules from other nucleic acid molecules based on any one of a series of physical properties. For example, the invention provides, in one aspect, methods for separating DNA from RNA comprising contacting a solid matrix with a sample which contains both DNA and RNA, followed by contacting the solid matrix with a washing solution. Nucleic acid molecules (e.g., DNA) which remain bound to the solid matrix may then be released by contacting the washed solid matrix with a releasing reagent of the invention.

As one skilled in the art would recognize, when plasmid DNA, for example, is sought, it will often be advantageous to treat the solid matrix containing the sample with a releasing reagent either without intervening washing or after a very brief washing (e.g., washing for about 3 seconds). Further, when eukaryotic genomic DNA (e.g., genomic DNA from plant or animal cells), for example, is sought, it will often be advantageous to wash the solid matrix containing the sample with one or more washing solutions or steps prior to contacting the matrix with a releasing reagent.

In one aspect, the invention provides methods for separating linear nucleic acid molecules (e.g., sheared chromosomal DNA) from closed, circular nucleic acid molecules (e.g., plasmids). Thus, the invention further provides methods for separating linear nucleic acid molecules from closed, circular nucleic acid molecules comprising contacting a solid matrix with a sample which contains both linear nucleic acid molecules and closed, circular nucleic acid molecules, followed by contacting the solid matrix with a washing solution. Nucleic acid molecules which remain bound to the solid matrix may then be released by contacting the washed solid matrix with a releasing reagent of the invention.

Further, because larger nucleic acid molecules associate more tightly with solid matrices than smaller nucleic acid molecules, the invention further provides methods for separating nucleic acid molecules which differ in size. Thus, the invention further provides methods for separating smaller nucleic acid molecules from larger nucleic acid molecules comprising contacting a solid matrix with a sample which contains both smaller nucleic acid molecules and larger nucleic acid molecules, followed by contacting the solid matrix with a washing solution. Nucleic acid molecules which remain bound to the solid matrix may then be released by contacting the washed solid matrix with a releasing reagent of the invention.

Washing conditions, for example, may be adjusted to facilitate the release of smaller nucleic acid molecules of specific sizes while the larger nucleic acid molecules remain adhered to, attached to, bound to (covalently or non-covalently), and/or associated with matrices. One example of a washing condition which can be adjusted is the length of time for which washing occurs. For example, solid matrices may be washed in a washing solution for about 1 second, about 5 seconds, about 10 seconds, about 20 seconds, about 30 seconds, about 45 seconds, about 1 minute, about 2 minutes, about 5 minutes, about 10 minutes, about 15 minutes, about 20 minutes, about 30 minutes, about 45 minutes, about 60 minutes, about 75 minutes, or about 90 minutes. As one skilled in the art would recognize, the effect that various washing conditions have on the release of nucleic acid molecules of various size can be readily assayed using, for example, gel electrophoresis. Thus, one skilled in the art can readily adjust washing conditions such that nucleic acid molecules of specific sizes are removed from solid matrices by washing and nucleic acid molecules of specific sizes remain associated with these matrices. Further, as noted above, nucleic acid molecules which remain associated with these matrices can later be removed from the matrices using releasing reagents of the invention.

The "larger nucleic acid molecules" referred to above may be of an average size of about 50 kilobases or larger (e.g., about 50, about 100, about 150, about 200, about 250, about 300, about 350, about 400, about 450, about 500, about 600, about 700, about 800, about 900, about 1,000, about 1,500, about 2,000, about 2,500, about 3,000, or about 4,000 kilobases). Further, the "smaller nucleic acid molecules" referred to above may have an average size of less than about 50 kilobases (e.g., about 1, about 5, about 10, about 20, or about 40 kilobases).

Similarly, the "larger nucleic acid molecules" referred to above may be of an average size of about 150 kilobases or larger (e.g., about 150, about 200, about 250, about 300, about 350, about 400, about 450, about 500, about 600, about 700, about 800, about 900, about 1,000, about 1,500, about 2,000, about 2,500, about 3,000, or about 4,000 kilobases) and the "smaller nucleic acid molecules" referred to above may have an average size of less than about 150 kilobases (e.g., about 1, about 5, about 10, about 20, about 40, about 80, about 100, about 120, or about 140 kilobases).

Additionally, the "larger nucleic acid molecules" referred to above may be of an average size of about 250 kilobases or larger (e.g., about 250, about 300, about 350, about 400, about 450, about 500, about 600, about 700, about 800, about 900, about 1,000, about 1,500, about 2,000, about 2,500, about 3,000, or about 4,000 kilobases) and the "smaller nucleic acid molecules" referred to above may have an average size of less than about 250 kilobases (e.g., about 1, about 5, about 10, about 20, about 40, about 80, about 100, about 120, about 140, about 160, about 180, about 200, about 220, or about 240 kilobases).

In addition, the "larger nucleic acid molecules" referred to above may be of an average size of about 500 kilobases or larger (e.g., about 500, about 600, about 700, about 800, about 900, about 1,000, about 1,500, about 2,000, about 2,500, about 3,000, or about 4,000 kilobases) and the "smaller nucleic acid molecules" referred to above may have an average size of less than about 500 kilobases (e.g., about 1, about 5, about 10, about 20, about 40, about 80, about 100, about 120, about 140, about 160, about 180, about 200, about 220, about 240, about 250, about 300, about 350, about 400, or about 450 kilobases).

Furthermore, the "larger nucleic acid molecules" referred to above may be of an average size of about 1,000 kilobases or larger (e.g., about 1,000, about 1,500, about 2,000, about 2,500, about 3,000, or about 4,000 kilobases) and the "smaller nucleic acid molecules" referred to above may have an average size of less than about 1,000 kilobases (e.g., about 1, about 5, about 10, about 20, about 40, about 80, about 100, about 120, about 140, about 160, about 180, about 200, about 220, about 240, about 250, about 300, about 350, about 400, about 450 kilobases, about 500, about 550, about 650 kilobases, about 750, about 850, or about 950 kilobases).

Further, when releasing reagents used in methods of the invention will not solubilize substantial quantities of cellular contaminants or nucleic acid molecules which one seeks to remove from the solid matrix, then no intervening treatment (e.g., washing) of the solid matrix will often be necessary prior to releasing agent treatment. One example of such a situation is when the sample is obtained from seed material. Seeds contain a considerable amount of carbohydrates. The releasing reagents of the invention do not result in the release of substantial amounts of seed carbohydrates from solid matrices. Thus, when the sample comprises seed materials, in many instances, the sample may be directly applied to the solid matrix and then treated with a releasing agent without intervening treatment. As a result, nucleic acid molecules are released from the solid matrix and most of the seed carbohydrates remain associated with the matrix.

The releasing reagents of the invention may be aqueous or non-aqueous. As one skilled in the art would recognize, different alkanol amines suitable for use in releasing reagents demonstrate different solubility properties in both aqueous and non-aqueous solutions. Further, the choice of solvent system will vary with the particular application, the sample, and the solid matrix. Examples of non-aqueous solvents which can be used in releasing reagents of the invention include ethanol, methanol, propanol, butanol, acetonitrile, dimethyl sulfoxide (DMSO), and N,N-dimethylformamide (DMF).

In one specific embodiment of methods of the invention, 2 mm FTA® paper punches, to which nucleic acid molecules are bound, are soaked for 20 minutes at 90–100° C. in a releasing reagent which contains, is an aqueous solution, 1% mono-ethanolamine at pH 11.0. In this embodiment, described in more detail below in Example 2, substantial quantities of nucleic acid molecules are released from the FTA® punches. As one skilled in the art would recognize, these methods may be modified to suit the particular application. Thus, in one general aspect, the invention relates to methods for removing nucleic acid molecules from solid matrices which comprise contacting these matrices with solutions comprising an alkanol amine under specified conditions for a specified period of time.

In specific embodiments, the alkanol amine (e.g., ethanolamine) concentration in the releasing reagent is in the range of from about 0.01% to about 5.0% (vol./vol.), from about 0.01% to about 4.0% (vol./vol.), from about 0.01% to about 3.0% (vol./vol.), from about 0.01% to about 2.0% (vol./vol.), from about 0.01% to about 1.0% (vol./vol.), from about 0.01% to about 0.9% (vol./vol.), from about 0.01% to about 0.8% (vol./vol.), from about 0.01% to about 0.5% (vol./vol.), from about 0.1% to about 5.0% (vol./vol.), from about 0.1% to about 4.0% (vol./vol.), from about 0.1% to about 3.0% (vol./vol.), from about 0.1% to about 2.0% (vol./vol.), from about 0.1% to about 1.0% (vol./vol.), from about 0.1% to about 0.9% (vol./vol.), from about 0.1% to about 0.8% vol./vol.), from about 0.1% to about 0.5% (vol./vol.), from about 0.2% to about 5.0% (vol./vol.), from about 0.2% to about 4.0% (vol./vol.), from about 0.2% to about 3.0% (vol./vol.), from about 0.2% to about 2.0% (vol./vol.), from about 0.2% to about 1.0% (vol./vol.), from about 0.2% to about 0.9% (vol./vol.), from about 0.2% to about 0.8% (vol./vol.), from about 0.2% to about 0.5% (vol./vol.), from about 0.4% to about 5.0% (vol./vol.), from about 0.4% to about 4.0% (vol./vol.), from about 0.4% to about 3.0% (vol./vol.), from about 0.4% to about 2.0% (vol./vol.), from about 0.4% to about 1.0% (vol./vol.), from about 0.4% to about 0.9% (vol./vol.), from about 0.4% to about 0.8% (vol./vol.), from about 0.4% to about 0.7% (vol./vol.), from about 0.8% to about 5.0% (vol./vol.), from about 0.8% to about 4.0% (vol./vol.), from about 0.8% to about 3.0% (vol./vol.), from about 0.8% to about 2.0% (vol./vol.), or from about 0.8% to about 1.0% (vol./vol.). The invention further includes releasing reagents which contain about 0.01% (vol./vol.), about 0.1% (vol./vol.), about 0.2% (vol./vol.), about 0.4% (vol./vol.), about 0.7% (vol./vol.), about 0.8% (vol./vol.), about 0.9% (vol./vol.), about 1.0% (vol./vol.), about 1.1% (vol./vol.), about 1.2% (vol./vol.), about 1.4% (vol./vol.), about 1.6% (vol./vol.), about 1.8% (vol./vol.), about 2.0% (vol./vol.), about 2.5% (vol./vol.), about 3.0% (vol./vol.), about 3.5% (vol./vol.), about 4.0% (vol./vol.), about 4.5% (vol./vol.), or about 5.0% (vol./vol.).

The alkanol amine concentration used will vary with a number of factors, including the particular alkanol amine, the solubility of non-nucleic acid compounds present in the sample, the pH of the releasing reagent, the incubation conditions (e.g., length of incubation period and incubation temperature), and the solid matrix used. One of ordinary skill in the art would know how to identify alkanol amine concentrations suitable for particular applications. Similarly, one of ordinary skill in the art would also know how to select alkanol amines suitable for particular applications.

The pH of releasing reagents of the invention can vary within, for example, the following ranges: from about 8.0 to about 14.0, from about 8.5 to about 14, from about 9.0 to about 14.0, from about 9.5 to about 14.0, from about 10.0 to about 14.0, from about 10.5 to about 14.0, from about 11 to about 14.0, from about 7.5 to about 13.5, from about 7.5 to about 13.0, from about 7.5 to about 12.5, from about 7.5 to about 12.0, from about 7.5 to about 11.5, from about 7.5 to about 11.0, from about 7.5 to about 10.5, from about 7.5 to about 10.0, from about 7.5 to about 9.5, from about 8.0 to about 12.0, from about 8.0 to about 11.5, from about 8.0 to about 11.0, from about 8.5 to about 14.0, from about 8.5 to about 13.0, from about 8.5 to about 12.5, from about 8.5 to about 12.0, from about 8.5 to about 11.5, from about 8.5 to about 11.0, from about 9.0 to about 12.0, from about 9.0 to about 11.5, from about 9.0 to about 11.0, and from about 9.0 to about 10.5. The invention further includes releasing reagents which have a pH of about 8.0, about 8.5, about 9.0, about 9.5, about 10.0, about 10.5, about 11.0, about 11.5, about 12.0, about 12.5, about 13.0, about 13.5, or about 14.0.

Alkanol amines suitable for use with the invention will often have the capacity to act as a buffer. Thus, in some instances it will be possible to dilute the alkanol amines used in the practice of the invention with a solvent (e.g., water) and directly adjust the pH using either an acid or a base. In other instances, it may be necessary, or desirable, to include a buffering agent (e.g., Tris, 2-[(Tris(hydroxymethyl) methyl)amino]-1-ethanesulfonic acid (TES), methylamine, CAPS, 4-(Cyclohexylamino)-1-butanesulfonic acid (CABS),2-(N-Cyclohexylamino)ethanesulfonic acid (CHES), Tricine, or Bicine) in the releasing reagent. Buffers suitable for use in releasing reagents of the invention can be obtained from commercial suppliers such as Sigma-Aldrich Corporation, 3050 Spruce Street, St. Louis, Mo. 63103 USA.

The methods of the invention can be performed by incubation of the solid matrix with a releasing reagent at a number of temperatures and for varying incubation times. For example, incubations may be performed at temperatures ranging from about 65° C. to about 100° C., about 70° C. to about 100° C., about 80° C. to about 100° C., about 90° C. to about 100° C., about 65° C. to about 90° C., about 70° C. to about 90° C., about 80° C. to about 90° C., about 65° C. to about 80° C., or about 70° C. to about 80° C. Further, incubations may be performed at temperature such as about 65° C., about 70° C., about 75° C., about 80° C., about 85° C., about 90° C., about 95° C., or about 100° C.

As noted above, the solid matrix from which nucleic acid release is desired can be incubated with the releasing reagent for various periods of time. As one skilled in the art would recognize, longer incubation periods will result in the release of nucleic acid molecules until an equilibrium is reached between the concentration of nucleic acid molecules in the releasing reagent and that bound to the solid matrix.

Solid matrices may be incubated with the releasing reagent for varying periods of time such as for 1 to 60 minutes, 5 to 50 minutes, 10 to 40 minutes, 20 to 30 minutes. 20 to 40 minutes, 30 to 50 minutes, 40 to 60 minutes, or 40 to 90 minutes. Further, incubations may be performed for about 1, 5, 10, 15, 20, 25, 30, 35, 40, 45, 50, 55, 60, 65, 70, 75, 80, 85, 90, 120, 180, or 240 minutes. Such incubation periods will often be useful when nucleic acid molecules are released from a solid matrix which is in sheet form.

Of course, the length of the incubation period used will vary with the particular conditions. Examples of conditions where relatively long incubation periods (e.g., eight hours, one day, two days, three days, five days, seven days) may be desirable include situations where the concentration of nucleic acid molecules on the solid matrix is low, the concentration of the alkanol amine is low (e.g., 0.1% ethanolamine), and/or the incubation temperature is low (e.g., 70° C. or lower).

Further, the length of the incubation period, as well as other incubation conditions, can be varied so that a particular amount or percentage of the nucleic acid molecules in the sample is released into the releasing reagent. For example, incubation conditions can be adjusted such that 0.5%, 5%,10%,20%, 30%,40%, 50%, 60%, 70%, 80%, or 90% of the nucleic acid molecules present on the solid matrix are released into the releasing reagent. One of ordinary skill in the art would know how to determine incubation conditions suitable for particular applications.

Tubular/column forms of solid matrices suitable for use in methods of the invention may have, for example, the following attributes. The solid matrix can be placed in a tube where it runs from one end to the other end, with room at one end (i.e., the top) for sample addition. In such embodiments, the solid matrix will generally extend from side wall to side wall within the tube. Thus, the majority of fluids which passes through the tube will have to pass through the solid matrix. In such situations, the solid matrix and tube can form a structure similar to that of columns used for chromatography. Thus, these solid matrix/tube formats are referred to as "solid matrix columns." As implied above, the solid matrix may form a solid or loose packing in these column forms.

As with the flat sheet embodiments of the invention, samples applied to solid matrix columns may be washed using solutions described above. Further, release of nucleic acid molecules from solid matrix columns may be induced by the passage of releasing reagents through columns. In one specific aspect of the invention, the matrix in the solid matrix column is washed at room temperature to remove contaminants. The bottom of the column is then plugged to prevent fluid flow, the column is heated to 95° C., and the releasing reagent (also heated to 90° C.) is then applied to the column. The bottom of the column is unplugged for sufficient time to allow the releasing reagent to fill the column and then replugged. After a 30 minute incubation at 95° C., the column in unplugged again and the releasing reagent with nucleic acid molecules is drained from the column. In one more specific aspect, the solid matrix columns are spin columns which can be placed in a centrifuge and the releasing reagent is removed from the columns by centrifugation.

As one skilled in the art would recognize, incubation conditions can be varied similar to the incubation conditions as described above. Further, the particular incubation conditions used will again vary with the sample, the nucleic acid molecules which are released from the solid matrix, and the solid matrix itself. One of ordinary skill in the art would know how to determine incubation conditions suitable for particular applications.

Nucleic acid molecules released from solid matrices may be used in or manipulated by one or more standard molecular biology techniques, such as nucleic acid synthesis, restriction endonuclease digestion, hybridization reactions, ligation to other nucleic acid molecules, sequencing, amplification (e.g., PCR), transformation, and transfection. Generally, the released nucleic acid molecules will be used after dilution with another solution (e.g., Tris-EDTA) to render the released/solubilized nucleic acid molecules suitable for the intended use (e.g., PCR).

The compositions and methods of the invention can be designed so that the nucleic acid molecules are released from solid matrices into a solution having a relatively low salt content. Further, as implied above, the salt concentration of the releasing reagent containing the nucleic acid molecules can be decreased by dilution. In situations where the salt content is higher than desired, the nucleic acid molecules can be desalted prior to use (e.g., the nucleic acid molecules can be separated from the alkanol amine) using standard techniques.

The invention further provides recombinant host cells which comprise nucleic acid molecules prepared by methods of the invention, as well as methods for preparing recombinant host cells comprising these nucleic acid molecules. Representative examples of appropriate hosts include bacterial cells (e.g., *Escherichia coli, Salmonella typhimurium*), fungal cells (e.g., *Saccharomyces cerevisiae, Schizosaccharomyces pombe, Neurospora crassa*), insect cells (e.g., Drosophila S2 cells, Spodoptera Sf9 cells), animal cells (e.g., CHO cells. COS cells, Bowes melanoma cells), and plant cells. Appropriate media and conditions for culturing the above-described host cells are known in the art.

Nucleic acid molecules prepared by methods of the invention may be introduced into host cells by methods described in standard laboratory manuals (see, e.g., Sambrook, J. et al, eds., MOLECULAR CLONING, A LABORATORY MANUAL, 2nd, edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997), Chapter 16), including methods such as electroporation, DEAE-dextran mediated transfection, transfection, microinjection, cationic lipid-mediated transfection, electroporation, transduction, scrape loading, ballistic introduction, and infection. Methods for the introduction of nucleic acid molecules into host cells are discussed, for example, in Felgner et al., U.S. Pat. No. 5,580,859.

Nucleic acid molecules prepared by methods of the invention may also contain genetic elements which allow for chromosomal integration of vector sequences. Such elements are useful for the stable maintenance of heterologous sequences and include sequences which confer both site-specific and site-independent integration. Site-specific integration (e.g., homologous integration) and site-independent integration, sometimes referred to as "random integration" can be used to introduce heterologous sequences of interest into host cell chromosomes. Descriptions and methods for inserting genetic material into eukaryotic chromosomes, for example, are available from numerous sources including Sambrook, J. et al., eds. (MOLECULAR CLONING, A LABORATORY MANUAL, 2nd. edition, Cold Spring Harbor Laboratory Press, Cold Spring Harbor, N.Y. (1989)).

III. Automated Sample Processing

The invention provides compositions, methods and reagents suitable for a number of applications, in addition to the purification and/or isolation of nucleic acid molecules from individual samples. One example of such an application is the purification and/or isolation of nucleic acid molecules derived from collections of samples which represent individual members of populations.

In one embodiment, samples comprising viral plaques (e.g., plaques of T4 phage) on plates are transferred to a solid matrix. Depending on the particular application, the solid matrix may then be either stored for later use or treated with a releasing reagent to release viral nucleic acid molecules. In many instances, the solid matrix will be cut into pieces which contain different nucleic acid molecules. This segmentation of the solid matrix may be random or may result in the production of individual pieces which contain, for example, nucleic acid molecules corresponding to particular viral plaques.

Similarly, samples from a variety of non-viral sources can be transferred to solid matrices and used to prepare individual nucleic acid molecules. For example, samples (e.g., bacterial cultures) which contain different nucleic acid molecules can be prepared in the individual wells of a 96 well plate (e.g. a 96 well MicroPlate). Portions of these samples can then be transferred to solid matrices using a DNA Card Registration Tool (Cat. No. VP 382CS) and Slot Pin Spotter (Cat. No. VP 408S5), available from V&P Scientific, Inc., 9823 Pacific Heights Boulevard, Suite T, San Diego, Calif. 92121 USA. Using this device, 5 µl from each of the 96 sample wells can be transferred at one time to an FTA® CloneSaver 96 Card, available from Invitrogen Corp., Life Technologies Division, 9800 Medical Center Drive, Rockville, Md. 20850 USA. Optionally, a dye (e.g., bromophenol blue) may be added to each of the sample wells to mark the sample location after application to the FTA® CloneSaver 96 Card.

Once samples have been applied to a solid matrix, such as an FTA® CloneSaver 96 Card, the solid matrix can be cut into pieces to separate the portions of the matrix to which individual samples have been applied. In situations where the sample has been applied in a specific pattern (e.g., where a DNA Card Registration Tool, a Slot Pin Spotter, and an FTA® CloneSaver 96 Card have been used as described above), a machine can be readily designed to cut the solid matrix in such a manner so as to separate individual samples. Using FTA® CloneSaver 96 Cards as an example, a machine can be designed which punches out portions of the card corresponding to some or all of the 96 positions which contain samples. These individual card pieces can then be placed in the individual wells of a 96 well plate and treated with various reagents to remove contaminants and release nucleic acid molecules. For example, reagents (e.g., washing solutions) may be added to each of the wells and then removed by aspiration. Further, the releasing reagent may be added to each of the wells and then removed by aspiration and transferred to another vessel. As one alternative, the solid matrices (e.g., the card pieces) can be removed from the wells after the incubation period, resulting in the nucleic acid molecules remaining behind. As another alternative, the solid matrices can be left in the wells with the released nucleic acid molecules. The most appropriate course of action will vary with the particular application(s) in which the nucleic acid molecules are intended to be used.

One specific application of automated methods of the invention is in the high-throughput amplification of nucleic acid molecules by PCR, followed by sequencing of amplification products. Systems can be designed so that each sample applied to solid matrices contains cells or plaques having different nucleic acid molecules.

Further, nucleic acid samples from which nucleic acid molecules can be released using compositions and methods of the invention can be conveniently prepared, stored, and sold, or otherwise transferred to individuals or entities, for use in methods of the invention.

In other specific embodiments of the invention, robotic systems perform essentially all of the steps required for determining genotypes using samples. In such applications, a sample card designed to hold 96 samples and having a reinforced backing may be used. This reinforced backing is advantageous because it increases the durability of the card and thus makes the card easier to handle by robotic systems.

A liquid handling system is used to deposit fluid containing the samples (e.g., 5 μl of each) at the appropriate locations on the sample card (e.g., an FTA® CloneSaver 96 Card). After the samples have dried, either the same or another machine cuts out portions of the card (e.g., 2 mm circles are punched out of the card) which contain the individual samples. These portions of the card are then placed by the machine into the wells of a 96 well plate. Reagents are added and removed from the wells using a liquid handler. Thermocycling, for example, can also be performed on the plates. Further, portions of fluid from the wells containing solubilized nucleic acid molecules can be removed and placed in other containers for use in restriction fragment length polymorphism (RFLP) or Southern blot analyses.

Processes of the invention are especially useful for generating genotype data using large numbers of samples. For example, genotype analyses of a large number of individuals can be performed using human blood in processes of the invention, followed by PCR using flourescent primers and by sequencing using automated sequencing machines.

Processes of the invention are also useful for genotype analysis of large numbers of samples obtained from plants, microorganisms and non-human animals. Using plants as an example, large numbers of plant samples can be prepared and screened from genetic properties associated with one or more genotypes. This will be especially useful for identifying particular genotypes of plants grown in specific geographic regions. For example, material from soybeans (e.g., leaves or seeds) may be collected from fields in a particular region. The plant material may be either applied directly to the solid matrix or may be dispersed into a solution prior to sample addition.

When plant material, or any other solid material, is applied directly to a solid matrix, it will generally be advantageous to apply the material to the matrix by the use of compression force. In other words, the solid material will often be crushed against the surface of the solid matrix.

A device may be employed for applying solid materials to solid matrices (e.g., a hammer). In one embodiment, this device contains a chamber, where the solid material containing the nucleic acid molecules is initially placed. An piston, or piston-like object, is located at one end of this chamber and the solid matrix is located at the other end. Thus, the movement of the piston, or piston-like object, towards the solid matrix results in the solid material being forced against the surface of the solid matrix. Nucleic acid molecules from the solid material are deposited on the solid matrix during this process. The device optionally has a solid portion which supports the back portion of the solid matrix and prevents the solid material from being forced through the matrix. This solid portion is not necessary when the solid matrix is rigid enough to withstand the pressure exerted by compression of the piston or piston-like object with damage to its structural integrity.

The above device especially is useful for the collection of plant material samples over a particular geographic region. The device will generally be relatively small, portable, and capable of being operated using manually induced pressure. Further, the device eliminates the need to prepare sample solutions for application to solid matrices. The device also provides uniform sample application on the surface of the solid matrix. Thus, in another aspect, the invention provides a device for the application of samples to solid matrices, wherein the device has (1) a chamber which houses solid materials containing nucleic acid molecules (i.e., the sample), (2) a piston, or piston-like object, at one end of the chamber, and (3) an attachment site for holding solid matrices at the other end of the chamber.

Plants which can be used in the methods of the invention include, but are not limited to, soybeans, corn, Rey, wheat, sorghum, rice, green peppers, red peppers, peas, pine trees, blue spruce, maple trees, grass (e.g., Kentucky Blue Grass), and cotton. Portions of plants which can be used in methods of the invention include stems, roots, seed, leaves, petals, and sepals.

The genotype analysis methods of the invention are useful for monitoring the spread of plant strains and genetic markers across geographic regions. These method are also useful for detecting genetically modified organisms (G.M.O.S). One example of a G.M.O. is a plant which has been grown from seeds derived from another G.M.O. Thus, the invention provides methods for identifying G.M.O.s comprising obtaining samples from plants, applying these samples to solid matrices, releasing nucleic acid molecules associated with the solid matrices, and analyzing the nucleic acid molecules to determine a genotype related to one genetic trait of the plant from which the sample was obtained. In related embodiments, genotypes related to multiple traits (e.g., two, three, four or five) may be determined.

When screening plant materials to identify/detect G.M.O.S, as well as specific plant strains, molecular marker detection methods will generally be used. For example, PCR can be performed to amplify nucleic acid molecules which represent single copy genes. These amplified nucleic acid molecules may then be analyzed using methods such as sequencing, RFLP analysis, or hybridization analysis to determine whether a particular plant is a G.M.O.

IV. Kits

Other embodiments of the invention, include kits for releasing nucleic acid molecules from solid matrices and kits for the purification and/or isolation of nucleic acid molecules. Kits serve to expedite the performance of, for example, methods of the invention by providing multiple components and reagents packaged together. Further, reagents of these kits can be supplied in pre-measured units so as to increase precision and reliability of the methods.

Kits of the invention for removing nucleic acid molecules from solid matrices will generally comprising a carton such as a box, one or more containers such as boxes, tubes, ampules, jars, bags, plates and the like, and one or more releasing reagents and one or more individual components selected from the group consisting of:

(a) at least one (e.g., one, two, three, four, five, ten, twenty, fifty, one hundred) solid matrix;

(b) at least one apparatus for applying samples to solid matrices;

(c) at least one apparatus for cutting solid matrices into sections which contain samples; and (d) at least one washing solution.

Apparatuses for applying samples to solid matrices include essentially any device which can be used for sample application. One example of such a device is a DNA Card Registration Tool and Slot Pin Spotter which, as noted above, can be used to apply 96 samples at one time to a solid matrix. Other examples include microcapillary tubes and pipettes (e.g., micropipettes such as a PIPETEMAN™), as well as other devices which can be used to transfer and/or deliver fluids. Yet other examples include the device described both below in Example 1 and above for applying solid material to solid matrices.

Apparatuses for cutting solid matrices into sections which contain samples include devices for cutting materials such as papers and cards. Examples of such devices include scissors, razors, knives, and the HARRIS MICRO PUNCH™ Apparatus. Devices such as HARRIS MICRO PUNCH™ Apparatuses are particularly useful because the can be used to cut solid matrices into circular pieces of relatively uniform size (e.g., 1.2 mm, 2 mm. etc.).

Washing solutions supplied with kits of the invention will vary with the particular application that the kit is intended for. As an example, when the kit is designed for the purification and/or isolation of high molecular weight nucleic acid molecules from samples which contain high concentrations of fats and lipids (e.g., adipose tissues), one or more washing solutions contained with the kit will generally contain a detergent (e.g., TRITON X-100).

Further, when multiple washing solutions are contained in the kit the solutions used for washing steps earlier in the washing process may contain agents which are removed by later washing steps. For example, when two washing steps are employed, the washing solution used in the first washing step may contain a detergent. The washing solution used in the second washing step, however, may not contain a detergent and may, in part, be used to remove the detergent added to the solid matrix by the first washing solution.

Examples of washing solutions which can be used with various embodiments of the invention include 10 mM Tris, 1 mM EDTA (pH 7.3); water; and solutions which contain detergents.

Sample containers and containers solid matrices may also be included in kits of the invention. One example a container suitable for use in a number of embodiments of the invention is a FTA® 96-well MicroPlate (Invitrogen Corp, Life Technologies Division, Cat. No. 10786-028). Plates such as these can be used, for examples, to house both the samples prior to application to solid matrices and pieces of solid matrices which contain samples.

Columns may also be included in kits of the invention (e.g., columns suitable for centrifugation in, for example, micro centrifuges). These columns may be used, for example, to desalt samples or to separate larger nucleic acid molecules from smaller molecules such as nucleotides, proteins, RNA, etc. Such columns are known in the art and may contain for example, material designed for molecular weight separations such as Sephadex® G-50.

It will be understood by one of ordinary skill in the relevant arts that ol her suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Pine needles from individual trees (*Pinus pinus*) are collected at various locations in the Shenandoah National Park. Needles from each tree are placed over the surface of an FTA® CloneSaver 96 Card and crushed into the Card using a hammer. The needles are placed in the Card such that each position on the card contains sample material from only one tree. As each sample is applied to the card, a log is kept so that the sample can be linked to a particular tree. Once samples have been applied to all of the sample positions on the card, the card is stored at ambient temperature until it is transported to a lab for analysis.

Once in the lab, the samples are "punched" from the FTA® card using a HARRIS MICRO PUNCH™ Apparatus with mat. The resulting 2 mm punches are then placed in wells of a 96 well plate and washed with Tris-EDTA (pH 7.3). 50 $\mu$l of ethanolamine, adjusted to pH 11.0 with KOH, is then added to each of the wells. After incubation at 90° C. for 30 minutes, the fluid in each well containing the released nucleic acid molecules is removed by aspiration, transferred to 0.5 ml microcentrifuge tubes, and frozen for later use in PCR reactions.

Example 2

Methods

Twenty-five $\mu$l of fresh blood was spotted onto individual locations of FTA® CloneSaver 96 Cards using a Model P-200 PIPETEMAN™ (Rainin Instrument Company, Inc. Rainin Road, Box 4026, Woburn, Mass., 01888). These Cards were stored at room temperature until used.

The releasing reagents were composed of ethanolamine diluted in water to a concentration of between 0.01% and 1%. The pH range was between 8.3 and 13. The pH was adjusted by the addition of aqueous KOH. The best results were obtained at a pH of 11 at a concentration of 1%. The ethanolamine reagents were compared to 15 mM and 30 mM CABS [4-(cyclohexylamino)-1-butane sulfonic acid] buffer, CAPS [3-(cyclohexylamino)-1-propane sulfonic acid] buffer, Gentra Elution Buffer 2 (used with the GENERATION™ CAPTURE COLUMN™ Kit, Gentra Systems Inc., 13355 10th Avenue N., Suite 120, Minneapolis, Minn. 55441, USA), and AmpDirect (Shimadzu, Inc., 1, Nishinokyo Kuwabaracho, Nakagyou-ku, Kyoto 604-8511, Japan).

After sample application, FTA® punches were washed with FTA® Purification Reagent (Invitrogen Corp., Life Technologies Division, Cat. No. 10876) and TE buffer according to manufacturer's recommendations.

Figure 4:
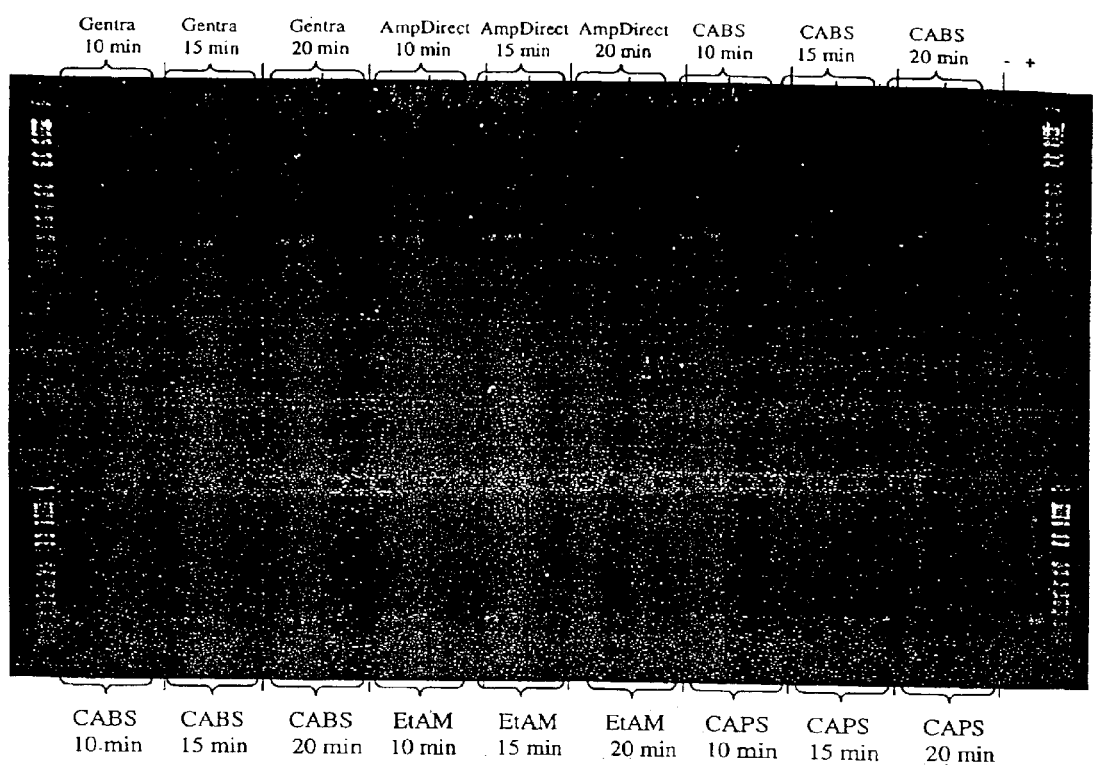
FIG. 4 depicts an agarose gel showing PCR performed on nucleic acid molecules released from FTA® paper using different reagents. Punches were heated for 10 minutes, 15 minutes, or 20 minutes in 0.2% ethanolamine, pH 11. PCR was performed as follows. Each 15 $\mu$l PCR reaction was performed using 1 $\mu$l of released DNA. The PCR reaction buffer contained 20 mM Tris-HCl (pH 8.4), 50 mM KCl, 1.5 mM MgCl$_2$, 200 $\mu$M dNTPs, 5 $\mu$l primer, 0.04 units of ®PLATLNUM® Taq DNA polymerase (Invitrogen Corp., Catalog No. 10966-018), and a primer set which amplifies D1S197 microsatellite marker DNA. Thermocycling was performed using the following temperature shifts: 80° C. for 10 minutes, and 94° C. for 1 minute; ten cycles of 94° C. for 30 seconds, 55° for 30 seconds, and 72° C. for 1 minute; twenty cycles of 89° C. for 30 seconds, 55° C. for 30 seconds, and 72° C. for 1 minute; and final extension of 72° C. for 10 minutes. PCR reaction products were stored at 4° C. until analyzed. Five µl of the PCR reaction was loaded onto an agarose gel. In addition, 5 µl of the PCR reaction diluted 1:10 was also loaded onto the gel in order to determine if there was a difference in the amount of product generated for each reagent tested. From this agarose gel, it was determined that the 0.2% ethanolamine performed as well as Gentra Elution Buffer 2. Both of these reagents had visible PCR products when diluted 1:10 (right of short dividing line on the gel photograph).
Figure 5:
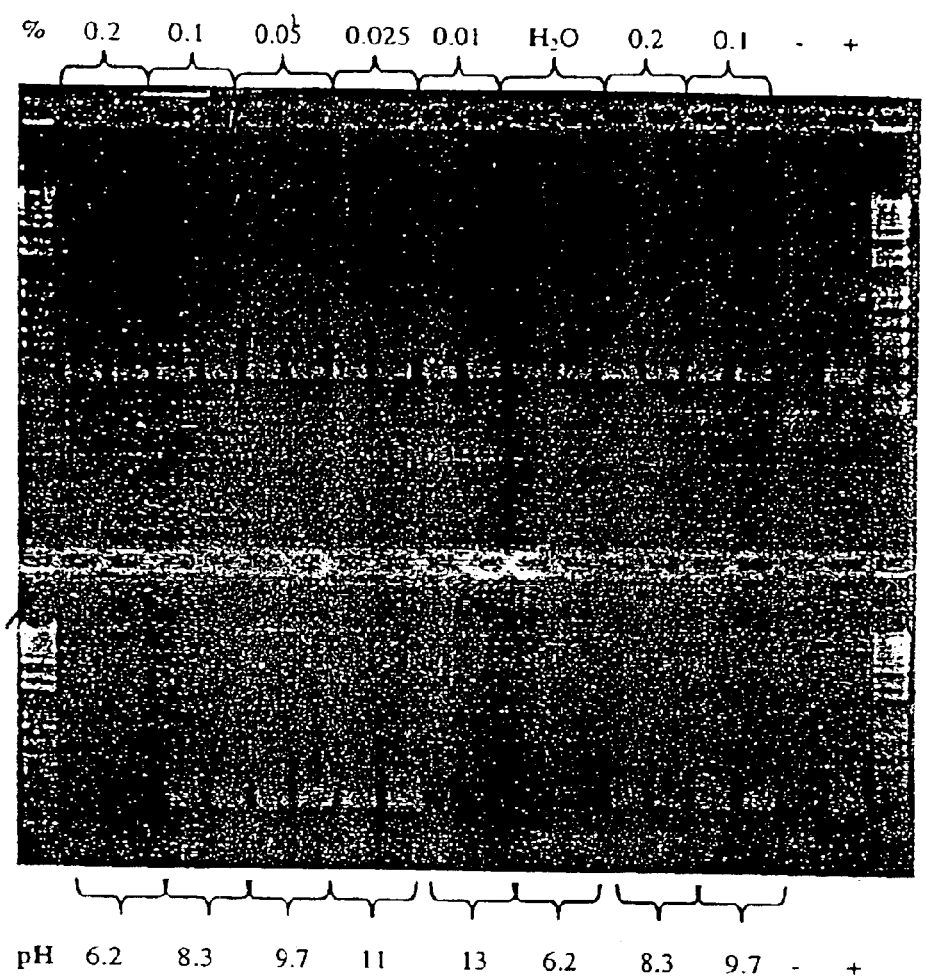
FIG. 5 depicts an agarose gel which shows the effect of releasing reagent ethanolamine concentration (%) and pH on the formation of PCR products. PCR was performed as described in FIG. 4 using 1 µl of released DNA in a 15 µl PCR reaction. 5 µl of the PCR reaction was loaded onto an agarose gel for electrophoresis. These results indicate that there is a slight increase in the amount of amplification seen when the concentration of ethanolamine is increased. The effect of pH is also clearly seen here. PCR products are generated at a pH range of 8.3 to 11. At pH 6.2 and 13 no PCR product is generated. These data support the previous data generated from the ACES quantitation kit regarding ethanolamine concentration and pH (see FIG. 3).
Figure 6:
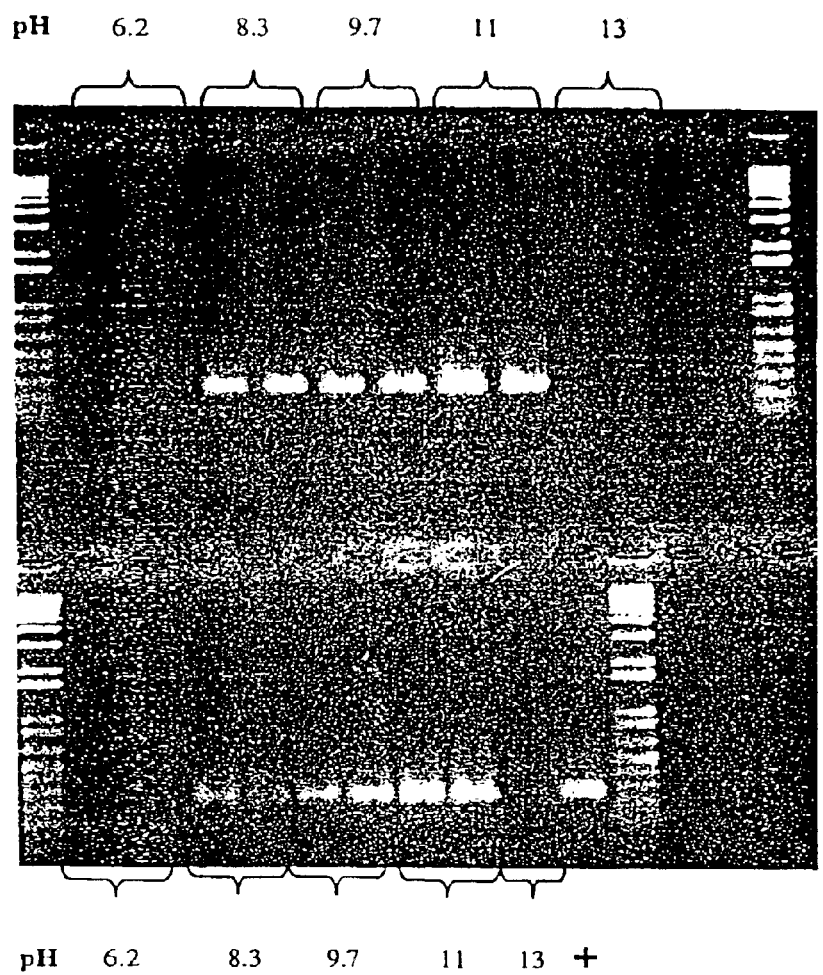
FIG. 6 depicts an agarose gel which shows the effect of releasing reagent pH on the formation of PCR products. PCR was performed as described in FIG. 4 using 1 µl of released DNA in a 15 µl PCR reaction. 5 µl of the PCR reaction was loaded onto an agarose gel for electrophoresis. No PCR product was generated at pH 6.2 and 13. The amount of PCR product produced increases with the pH. These data support the data shown above in FIG. 2, which indicate that greater quantities of DNA are released as the pH of the releasing reagent is increased from 8.3 to 11. From this it can be concluded that the most effective pH for releasing DNA from the FTA® paper is pH 11.

The releasing reagents were added at 50 $\mu$l/2 mm punch. The punches were then heated to 90–100° C. for 1–30 minutes, with the best results being obtained between 10 and 20 minutes based on PCR analysis. This conclusion was based on the results obtained in FIGS. 1 and 3. FIG. 1 shows that as much as 100 pg/ml is released after 10 minutes. At 20 minutes approximately 1 ng/ml is released using the releasing reagent. FIG. 4 shows that the PCR results obtained using the released DNA is similar after heating for 10, 15 or 20 minutes. However, when the PCR product is diluted 1:10 differences in the amount of product is noticeable. The Gentra Elution Buffer 2 and the ethanolamine releasing reagent perform better that the other reagents tested. PCR products are clearly visible for the 15 and 20 minute heating times when the PCR reaction is diluted 1:10 prior to loading on the gel.

The concentration of the released DNA was determined using the ACES™ 2.0+ Human DNA Quantitation System. In this system 10 $\mu$l of released DNA is used for quantitation. Following quantitation the performance of each released DNA was tested for its ability to produce amplified products when used in genotyping PCR assays. This was tested by setting up a standard genotyping PCR assay and then adding 1 $\mu$l of the released DNA to be tested. Each PCR assay was in a total volume of 15 $\mu$l. The PCR products were analyzed by electrophoresis on a 1.5% agarose gel. Electrophoresis was performed at 100 volts for 1 hour. The gels were then stained with ethidium bromide and a photograph was taken.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for removing nucleic acid molecules from a solid matrix comprising contacting the solid matrix with a releasing reagent, wherein the releasing reagent comprises one or more alkanol amines; and the solid matrix comprises uric acid or a urate salt.

2. The method of claim 1, wherein the solid matrix is a cellulose based matrix or a micromesh synthetic plastic matrix comprising said uric acid or a urate salt.

3. A method for removing nucleic acid molecules from a solid matrix comprising contacting the solid matrix with a releasing reagent, wherein the releasing reagent comprises one or more alkanol amines; and the solid matrix is a filter paper.

4. The method of claim 3, wherein the solid matrix is FTA® paper.

5. A method for removing nucleic acid molecules from a solid matrix comprising contacting the solid matrix with a releasing reagent, wherein the releasing reagent comprises more than one ethanolamine.

6. The method of claim 3, wherein one or more alkanol amines is an ethanolamine.

7. The method of claim 5, wherein one of said more than one ethanolamine is mono-ethanolamine.

8. The method of claim 5, wherein one of said more than one ethanolamine is di-ethanolamine.

9. The method of claim 5, wherein one of said more than one ethanolamine is tri-ethanolamine.

10. The method of claim 3, wherein the releasing reagent is an aqueous solution comprising said one or more alkanol amines.

11. The method of claim 3, wherein the releasing reagent has a pH from about 8.3 to about 13.

12. The method of claim 11, wherein the releasing reagent has a pH from about 10 to about 12.

13. The method of claim 12, wherein the releasing reagent has a pH of about 11.

14. The method of claim 3, wherein the concentration of said one or more alkanol amines is from about 0.01% to about 5% (vol./vol.).

15. The method of claim 14, wherein the concentration of said one or more alkanol amines is from about 0.01% to about 3% (vol./vol.).

16. The method of claim 15, wherein the concentration of said one or more alkanol amines is from about 0.01% to about 1% (vol./vol.).

17. The method of claim 16, wherein the concentration of said one or more alkanol amines is from about 0.1% to about 1% (vol./vol.).

18. The method of claim 3, wherein the solid matrix is incubated with the releasing reagent for about 1 to about 180 minutes.

19. The method of claim 18, wherein the solid matrix is incubated with the releasing reagent for about 1 to about 120 minutes.

20. The method of claim 19, wherein the solid matrix is incubated with the releasing reagent for about 10 to about 60 minutes.

21. The method of claim 20, wherein the solid matrix is incubated with the releasing reagent for about 10 to about 30 minutes.

22. A method for removing nucleic acid molecules from a solid matrix comprising contacting the solid matrix with a releasing reagent, wherein the releasing reagent comprises one or more alkanol amines; and the solid matrix is incubated with the releasing reagent at about 65° C. to about 100° C.

23. The method of claim 22, wherein the solid matrix is incubated with the releasing reagent at about 90° C. to about 100° C.

24. The method of claim 22, which further comprises separating the nucleic acid molecules from the releasing reagent.

25. The method of claim 22, wherein the nucleic acid molecules comprise DNA.

26. The method of claim 22, wherein the nucleic acid molecules comprise a vector.

27. The method of claim 26, wherein the vector comprises a plasmid or an artificial chromosome.

28. The method of claim 22, wherein the nucleic acid molecules are from a cell or a virus.

29. A method of isolating a nucleic acid molecule comprising:

(a) contacting the nucleic acid molecule with a solid matrix under conditions which favor adherence, attachment, association, and/or binding of the nucleic acid molecule to the solid matrix; and (b) contacting the solid matrix containing the bound nucleic acid molecule with a releasing reagent comprising one or more alkanol amines, under conditions which favor release of the nucleic acid molecule from the solid matrix, wherein the solid matrix comprises uric acid or a urate salt.

30. The method of claim 29, which further comprises collecting the releasing reagent containing the released nucleic acid molecule.

31. The method of claim 29, wherein the solid matrix is a cellulose based matrix or a micromesh synthetic plastic matrix comprising said uric acid or a urate salt.

32. A method of isolating a nucleic acid molecule comprising:

(a) contacting the nucleic acid molecule with a solid matrix under conditions which favor adherence, attachment, association, and/or binding of the nucleic acid molecule to the solid matrix; and (b) contacting the solid matrix containing the bound nucleic acid molecule with a releasing reagent comprising one or more alkanol amines, under conditions which favor release of the nucleic acid molecule from the solid matrix;

wherein the solid matrix is a filter paper.

33. The method of claim 32, wherein the solid matrix is FTA® paper.

34. A method of isolating a nucleic acid molecule comprising:

(a) contacting the nucleic acid molecule with a solid matrix under conditions which favor adherence, attachment, association, and/or binding of the nucleic acid molecule to the solid matrix; and (b) contacting the solid matrix containing the bound nucleic acid molecule with a releasing reagent, under conditions which favor release of the nucleic acid molecule from the solid matrix;

wherein the releasing reagent comprises more than one ethanolamine.

35. The method of claim 32, wherein the releasing reagent comprises an ethanolamine.

36. The method of claim 34, wherein the releasing reagent is an aqueous solution.

37. The method of claim 34, wherein the releasing reagent has a pH from about 8.3 to about 13.

38. The method of claim 37, wherein the releasing reagent has a pH from about 10 to about 12.

39. The method of claim 38, wherein the releasing reagent has a pH of about 11.

40. The method of claim 34, wherein the concentration of said more than one alkanol amines is from about 0.01% to about 5% (vol./vol.).

41. The method of claim 40, wherein the concentration of said more than one alkanol amines is from about 0.01% to about 3% (vol./vol.).

42. The method of claim 41, wherein the concentration of said more than one alkanol amines is from about 0.01% to about 1% (vol./vol.).

43. The method of claim 42, wherein the concentration of said more than one alkanol amines is from about 0.1% to about 1% (vol./vol.).

44. The method of claim 34, wherein the solid matrix is incubated with the releasing reagent for about 1 to about 180 minutes.

45. The method of claim 44, wherein the solid matrix is incubated with the releasing reagent for about 1 to about 120 minutes.

46. The method of claim 45, wherein the solid matrix is incubated with the releasing reagent for about 10 to about 60 minutes.

47. The method of claim 46, wherein the solid matrix is incubated with the releasing reagent for about 10 to about 30 minutes.

48. A method of isolating a nucleic acid molecule comprising:

(a) contacting the nucleic acid molecule with a solid matrix under conditions which favor adherence, attachment, association, and/or binding of the nucleic acid molecule to the solid matrix;

(b) contacting the solid matrix containing the bound nucleic acid molecule with a releasing reagent comprising one or more alkanol amines, under conditions which favor release of the nucleic acid molecule from the solid matrix; and wherein the solid matrix is incubated with the releasing reagent at about 65° C. to about 100° C.

49. The method of claim 48, wherein the solid matrix is incubated with the releasing reagent at about 90° C. to about 100° C.

50. The method of claim 34, which further comprises separating the nucleic acid molecules from the releasing reagent.

51. The method of claim 34, wherein the nucleic acid molecules comprises DNA.

52. The method of claim 34, wherein the nucleic acid molecules comprises a vector.

53. The method of claim 52, wherein the vector comprises a plasmid or an artificial chromosome.

54. The method of claim 34, wherein the nucleic acid molecules is from a cell or a virus.

55. The method of claim 34, wherein the nucleic acid molecules is amplified by PCR.

56. A method for separating RNA from DNA comprising:

(a) contacting a solid matrix with a sample which contains RNA and DNA;

(b) contacting the solid matrix of (a) with a washing solution under conditions sufficient to remove the RNA while the DNA is retained; and (c) contacting the washed solid matrix with a releasing reagent comprising one or more alkanol amines, under conditions which favor release of the DNA from the solid matrix, wherein the solid matrix is filter paper.

57. The method of claim 56, wherein the washing solution comprises either water or 10 mM Tris-HCl, 1 mM EDTA (pH 7.3).

58. The method of claim 56, wherein the solid matrices are contacted with the washing solution for a washing time ranging from 1 second to 90 minutes.

59. The method of claim 58, wherein the washing time is selected from the group consisting of:

(a) about 5 seconds;
(b) about 20 seconds;
(c) about 30 seconds;
(d) about 45 seconds;
(e) about 1 minute;
(f) about 5 minutes;
(g) about 10 minutes; and
(h) about 30 mintues.

60. A method for separating closed, circular nucleic acid molecules from linear nucleic acid molecules comprising:

(a) contacting a solid matrix with a sample which contains closed, circular nucleic acid molecules and linear nucleic acid molecules;

(b) contacting the solid matrix of (a) with a washing solution under conditions sufficient to remove closed, circular nucleic acid molecules while linear nucleic acid molecules are retained; and (c) contacting the washed solid matrix with a releasing reagent comprising one or more alkanol amines, under conditions which favor release of the linear nucleic acid molecules from the solid matrix, wherein the solid matrix is filter paper.

61. The method of claim 60, wherein the washing solution comprises either water or 10 mM Tris-HCl, 1 mM EDTA (pH 7.3).

62. The method of claim 60, wherein the solid matrix is contacted with the washing solution for a washing time ranging from 1 second to 90 minutes.

63. The method of claim 62, wherein the washing time is selected from the group consisting of:

(a) about 5 seconds;
(b) about 20 seconds;
(c) about 30 seconds;
(d) about 45 seconds;
(e) about 1 minute;
(f) about 5 minutes;
(g) about 10 minutes; and
(h) about 30 minutes.

64. A method for separating nucleic acid molecules by size comprising:

(a) contacting a solid matrix with a sample which contains nucleic acid molecules of different sizes;

(b) contacting the solid matrix of (a) with a washing solution under conditions sufficient to remove smaller nucleic acid molecules while larger nucleic acid molecules are retained; and (c) contacting the washed solid matrix with a releasing reagent comprising one or more alkanol amines, under conditions which favor release of the larger nucleic acid molecules from the solid matrix, wherein the solid matrix is filter paper.

65. The method of claim 64, wherein the washing solution comprises either water or 10 mM Tris-HCl, 1 mM EDTA (pH 7.3).

66. The method of claim 64, wherein the solid matrix is contacted with the washing solution for a washing time ranging from 1 second to 90 minutes.

67. The method of claim 66, wherein the washing time is a time selected from the group consisting of:

(a) about 5 seconds;
(b) about 20 seconds;
(c) about 30 seconds;
(d) about 45 seconds;
(e) about 1 minute;
(f) about 5 minutes;
(g) about 10 minutes; and
(h) about 30 minutes.

68. The method of claim 34, wherein one of said more than one ethanolamine is mono-ethanolamine, di-ethanolamine or tri-ethanolamine.

69. The method of claim 56, wherein the solid matrix is FTA® paper.

70. The method of claim 56, wherein one of said one or more alkanol amines is an ethanolamine.

71. The method of claim 70, wherein said ethanolamine is mono-ethanolamine, di-ethanolamine or tri-ethanolamine.

72. The method of claim 60, wherein the solid matrix is FTA® paper.

73. The method of claim 60, wherein one of said one or more alkanol amines is an ethanolamine.

74. The method of claim 73, wherein said ethanolamine is mono-ethanolamine, di-ethanolamine or tri-ethanolamine.

75. The method of claim 64, wherein the solid matrix is FTA® paper.

76. The method of claim 64, wherein one of said one or more alkanol amines is an ethanolamine.

77. The method of claim 76, wherein said ethanolamine is mono-ethanolamine, di-ethanolamine or tri-ethanolamine.

* * * * *